(12) United States Patent
Zalipsky

(10) Patent No.: US 6,342,244 B1
(45) Date of Patent: Jan. 29, 2002

(54) RELEASABLE LINKAGE AND COMPOSITIONS CONTAINING SAME

(75) Inventor: Samuel Zalipsky, Redwood City, CA (US)

(73) Assignee: Alza Corporation, Mountain View, CA (US)

(*) Notice: Subject to any disclaimer, the term of this patent is extended or adjusted under 35 U.S.C. 154(b) by 0 days.

(21) Appl. No.: 09/556,056

(22) Filed: Apr. 21, 2000

Related U.S. Application Data

(60) Provisional application No. 60/130,897, filed on Apr. 23, 1999, now abandoned.

(51) Int. Cl.[7] .................. A61K 9/127; A61K 45/00; A61K 38/00; A01N 61/00; C25D 3/60
(52) U.S. Cl. .................. 424/450; 424/85.1; 205/254; 514/1; 530/336; 536/84
(58) Field of Search .................. 424/85.1, 450; 205/254; 514/1; 530/336; 536/84

(56) References Cited

U.S. PATENT DOCUMENTS

| | | | |
|---|---|---|---|
| 4,179,337 A | 12/1979 | Davis et al. | 435/181 |
| 4,766,106 A | 8/1988 | Katre et al. | 514/12 |
| 4,902,502 A | 2/1990 | Nitecki et al. | 424/83 |
| 4,917,888 A | 4/1990 | Katre et al. | 424/85.91 |
| 4,935,465 A | 6/1990 | Garman | 525/54.1 |
| 5,103,556 A | 4/1992 | Filip et al. | 29/825 |
| 5,395,619 A | 3/1995 | Zalipsky et al. | 424/450 |
| 5,631,018 A | 5/1997 | Zalipsky et al. | 424/450 |

FOREIGN PATENT DOCUMENTS

| WO | WO 98/16201 | 4/1998 |
|---|---|---|

OTHER PUBLICATIONS

Brois, S. J. Et Al., "A New Pathway to Unsymmetrical Disulfides., " J. Amer. chem. Soc., vol. 92 (No. 26), p. 7629–7631, (Dec. 30, 1970).

Dittmer, J. C. Et Al., "A Simple, Specific Spray for the Detection of ... ," J. Lipid Res., pp. 126–127, (Jun. 14, 1964).

Grice, R. Et Al., "Cytotoxic Compounds. Part IV," J. Chem. Soc., pp. 1947–1954, (Jun. 14, 1963).

Kaneko, T. Et Al., "New Hydrazone Derivatives of Adriamycin and ... ," Bioconjugate Chem., vol. 2 (No. 3), pp. 133–141, (Jun. 14, 1991).

Lash, L. H. Et Al., "Distribution of Oxidized and Reduced Forms of Glutathione... ," Arch. Biochem. Biophys., Academic Press Inc., vol. 240 (No. 2), pp. 583–592, (Aug. 1, 1985).

Veronese Et Al., "Surface Modification of Proteins," Applied Biochem. and Biotech., pp. 141–152, (Jun. 14, 1985).

Zalipsky Et Al., "Evaluation of a New Reagent for Covalent Attachment..." Biotechnol. Appl. Biochem., pp. 100–114, (Jun. 14, 1992).

Zalipsky Et Al., "Attachment of Drugs to Polyethylene Glycols," Eur. Polymer. J., Pergamon Press Ltd. (Great Britain), vol. 19 (No. 12), pp. 1177–1183, (Jun. 14, 1983).

Zalipsky Et Al., "Synthesis of an End–Group Functionalized... ," Bioconj. Chem., American Chemical Society, vol. 4 (No. 4), pp. 296–299, (Jun. 14, 1993).

*Primary Examiner*—Jezia Riley
(74) *Attorney, Agent, or Firm*—Judy M. Mohr; Jacqueline F. Mahoney; Paul B. Simboli

(57) ABSTRACT

A compound comprised of a hydrophilic polymer covalently yet reversibly linked to a amine-containing ligand through a dithiobenzyl linkage is described.

47 Claims, 16 Drawing Sheets

RELEASABLE LINKAGE AND COMPOSITIONS CONTAINING SAME

This application claims the benefit of U.S. provisional Application No. 60/130,897, filed Apr. 23, 1999, abandoned, incorporated herein by reference in its entirety.

FIELD OF THE INVENTION

The present invention relates to a compound comprised of a hydrophilic polymer, such as polyethyleneglycol, cleavably linked to an amine-containing ligand, which in preferred embodiments can be an amine-containing lipid, drug or protein. The compounds are cleavable under mild thiolytic conditions to regenerate the amine-containing ligand in its original form.

BACKGROUND OF THE INVENTION

Hydrophilic polymers, such as polyethylene glycol (PEG), have been used for modification of various substrates, such as polypeptides, drugs and liposomes, in order to reduce immunogenicity of the substrate and/or to improve its blood circulation lifetime.

For example, parenterally administered proteins can be immunogenic and may have a short pharmacological half-life. Proteins can also be relatively water insoluble. Consequently, it can be difficult to achieve therapeutically useful blood levels of the proteins in patients. Conjugation of PEG to proteins has been described as an approach to overcoming these difficulties. Davis et al. in U.S. Pat. No. 4,179,337 disclose conjugating PEG to proteins such as enzymes and insulin to form PEG-protein conjugates having less immunogenicity yet which retain a substantial proportion of physiological activity. Veronese et al. (*Applied Biochem. and Biotech*, 11:141–152 (1985)) disclose activating polyethylene glycols with phenyl chloroformates to modify a ribonuclease and a superoxide dimutase. Katre et al. in U.S. Pat. Nos. 4,766,106 and 4,917,888 disclose solubilizing proteins by polymer conjugation. PEG and other polymers are conjugated to recombinant proteins to reduce immunogenicity and increase half-life. (Nitecki et al., U.S. Pat. No. 4,902,502; Enzon, Inc., PCT/US90/02133). Garman (U.S. Pat. No. 4,935,465) describes proteins modified with a water soluble polymer joined to the protein through a reversible linking group.

However, PEG-protein conjugates described to date suffer from several disadvantages. For example, modification of the protein with PEG often inactivates the protein so that the resulting conjugate has poor biological activity. Typically in the prior art to date, it is desired to have the PEG stably linked to the protein so that the beneficial properties provided by PEG remain. Another problem with some protein PEG conjugates is that upon decomposition of the conjugate undesirable products may be formed.

PEG has also been described for use in improving the blood circulation lifetime of liposomes (U.S. Pat. No. 5,103,556). Here, the PEG is covalently attached to the polar head group of a lipid in order to mask or shield the liposomes from being recognized and removed by the reticuloendothelial system. Liposomes having releasable PEG chains have also been described, where the PEG chain is released from the liposome upon exposure to a suitable stimulus, such as a change in pH (PCT/US97/18813). However, release of the PEG chain from the liposome suffers from the drawback that the decomposition products are chemically modified and can have unpredictable, potentially negative effects in vivo.

SUMMARY OF THE INVENTION

Accordingly, it is an object of the invention to provide a compound where a ligand is covalently yet reversibly linked to a hydrophilic polymer. Upon cleavage of the linkage, the ligand in its native form is regenerated.

In one aspect, the invention includes a compound having the general structure:

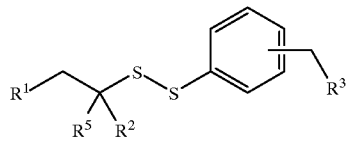

wherein $R^1$ is a hydrophilic polymer comprising a linkage for attachment to the dithiobenzyl moiety; $R^2$ is selected from the group consisting of H, alkyl and aryl; $R^3$ is selected from the group consisting of $O(C{=}O)R^4$, $S(C{=}O)R^4$, and $O(C{=}S)R^4$; $R^4$ comprises an amine-containing ligand; and $R^5$ is selected from the group consisting of H, alkyl and aryl; and where orientation of $CH_2$—$R^3$ is selected from the ortho position and the para position.

In one embodiment, $R^5$ is H and $R^2$ is selected from the group consisting of $CH_3$, $C_2H_5$ and $C_3H_8$. In another embodiment, $R^2$ and $R^5$ are alkyls.

In another embodiment, the amine-containing ligand $R^4$ is selected from the group consisting of a polypeptide, an armine-containing drug and an amine-containing lipid. In an embodiment where the amine-containing ligand $R^4$ is an amine-containing lipid, the lipid includes either a single hydrocarbon tail or a double hydrocarbon tail. In one preferred embodiment, the lipid is a phospholipid having a double hydrocarbon tail.

The hydrophilic polymer $R^1$ can be, in yet another embodiment, selected from the group consisting of polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide, copolymers thereof, and polyethyleneoxide-polypropylene oxide.

In one preferred embodiment, the hydrophilic polymer $R^1$ is polyethyleneglycol. In another embodiment, when $R^1$ is polyethylene glycol, $R^5$ is H and $R^2$ is $CH_3$ or $C_2H_5$.

In still another embodiment, the amine-containing ligand $R^4$ is a polypeptide. The polypeptide can be, in another embodiment, a recombinant polypeptide. Exemplary and preferred polypeptides include cytokines, such as interferons, interleukins, and growth factors, and enzymes.

In another aspect, the invention includes a composition comprising a conjugate obtainable by reaction with a compound having the general structural formula:

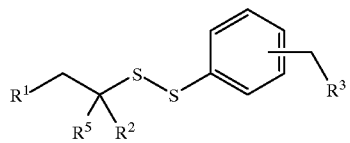

wherein $R^1$ is a hydrophilic polymer comprising a linkage for attachment to the dithiobenzyl moiety; $R^2$ is selected from the group consisting of H, alkyl and aryl; $R^3$ is selected from the group consisting of O(C=O)$R^4$, S(C=O)$R^4$, and O(C=S)$R^4$; $R^4$ comprises a leaving group; and $R^5$ is selected from the group consisting of H, alkyl and aryl; and where orientation of $CH_2$—$R^3$ is selected from the ortho position and the para position. The composition also includes a pharmaceutically-acceptable carrier, such as saline, buffer or the like.

In one embodiment of this aspect, $R^2$ is selected from the group consisting of $CH_3$, $C_2H_5$ and $C_3H_8$.

In another embodiment, $R^3$ is O(C=O)$R^4$ and $R^4$ is a hydroxy- or oxy-containing leaving group. The leaving group, in another embodiment, is derived from a compound selected from the group consisting of chloride, para-nitrophenol, ortho-nitrophenol, N-hydroxy-tetrahydrophthalimide, N-hydroxysuccinimide, N-hydroxyglutarimide, N-hydroxynorbornene-2,3-dicarboxyimide, 1-hydroxybenzotriazole, 3-hydroxypyridine, 4-hydroxypyridine, 2-hydroxypyridine, 1-hydroxy-6-trifluoromethylbenzotriazole, immidazole, triazole, N-methyl-imidazole, pentafluorophenol, trifluorophenol and trichlorophenol.

In one embodiment, the claimed compound is reacted with an amine-containing ligand that displaces $R^4$ to form a conjugate that includes the amine-containing ligand. For example, the amine-containing ligand can be a phospholipid.

In a preferred embodiment, the hydrophilic polymer $R^1$ is polyethyleneglycol, $R^5$ is H and $R^2$ is $CH_3$ or $C_2H_5$.

In yet another aspect of this embodiment, the composition containing the conjugate comprises a liposome. The liposome can further comprise an entrapped therapeutic agent.

In another embodiment, the amine-containing ligand comprises a polypeptide.

In yet another aspect, the invention includes a liposome composition comprising liposomes which include a surface coating of hydrophilic polymer chains wherein at least a portion of the hydrophilic polymer chains have the general structure:

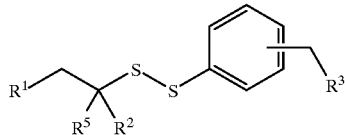

wherein $R^1$ is a hydrophilic polymer comprising a linkage for attachment to the dithiobenzyl moiety; $R^2$ is selected from the group consisting of H, alkyl and aryl; $R^3$ is selected from the group consisting of O(C=O)$R^4$, S(C=O)$R^4$, and O(C=S)$R^4$; $R^4$ comprises an amine-containing ligand; and $R^5$ is selected from the group consisting of H, alkyl and aryl; and where orientation of $CH_2$—$R^3$ is selected from the ortho position and the para position. The liposomes have a longer blood circulation lifetime than liposomes having hydrophilic polymer chains joined to the liposome via an aliphatic disulfide linkage.

In one embodiment, the liposome further comprises an entrapped therapeutic agent.

In still another aspect, the invention includes a method for improving the blood circulation lifetime of liposomes having a surface coating of releasable hydrophilic polymer chains. The method includes preparing liposomes that have between about 1% to about 20% of a compound having the general structure:

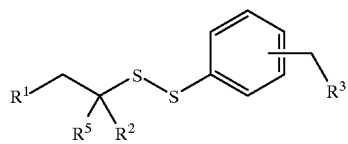

wherein $R^1$, $R^2$, $R^3$, and R are as described above and $R^4$ comprises an amine-containing lipid.

In a preferred embodiment of this aspect, $R^5$ is H and $R^2$ is selected from the group consisting of $CH_3$, $C_2H_5$ and $C_3H_8$.

In another embodiment, the amine-containing lipid comprises a phospholipid and $R^1$ is polyethyleneglycol.

In this aspect, the liposomes can further comprise an entrapped therapeutic agent.

These and other objects and features of the invention will be more fully appreciated when the following detailed description of the invention is read in conjunction with the accompanying drawings.

DETAILED DESCRIPTION OF THE INVENTION

I. Definitions

Figure 1A:
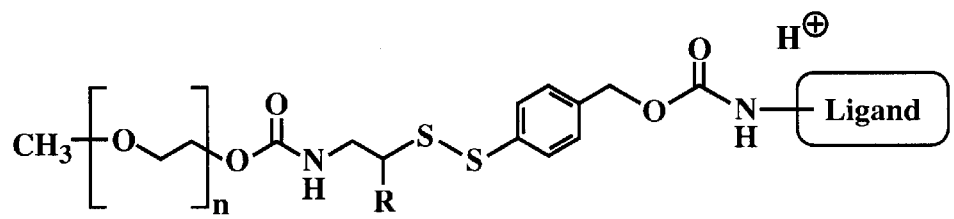
FIG. 1A shows an embodiment of the invention where the dithiobenzyl (DTB) links a methoxy-polyethyelene glycol (mPEG) moiety and the amine-containing ligand.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations, and the like.

"Amine-containing" intends any compound having a moiety derived from ammonia by replacing one or two of the hydrogen atoms by alkyl or aryl groups to yield general structures $RNH_2$ (primary amines) and $R_2NH$ (secondary amines), where R is any hydrocarbyl group.

"Hydrophilic polymer" as used herein refers to a polymer having moieties soluble in water, which lend to the polymer some degree of water solubility at room temperature. Exemplary hydrophilic polymers include polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethyleneglycol, polyaspartamide, copolymers of the above-recited polymers, and polyethyleneoxide-polypropylene oxide copolymers. Properties and reactions with many of these polymers are described in U.S. Pat. Nos. 5,395,619 and 5,631,018.

"Polymer comprising a reactive functional group" or "polymer comprising a linkage for attachment" refers to a polymer that has been modified, typically but not necessarily, at a terminal end moiety for reaction with another compound to form a covalent linkage. Reaction schemes to functionalize a polymer to have such a reactive functional group of moiety are readily determined by those of skill in the art and/or have been described, for example in U.S. Pat. No. 5,613,018 or by Zalipsky et al., in for example, *Eur. Polymer. J.*, 19(12):1177–1183 (1983); *Bioconj. Chem.*, 4(4):296–299 (1993).

"Recombinant" as in "recombinant polypeptide" implies joining of amino acids through laboratory manipulation into a desired sequence.

"Alkyl" as used herein intends a group derived from an alkane by removal of a hydrogen atom from any carbon atom: "$C_nH_{2n+1}$". The groups derived by removal of a hydrogen atom from a terminal carbon atom of unbranched alkanes form a subclass of normal alkyl (n-alkyl) groups: $H[CH_2]_n$—. The groups $RCH_2$—, $R_2CH$— (R not equal to H), and $R_3C$— (R not equal to H) are primary, secondary and tertiary alkyl groups respectively.

"Aryl" refers to a substituted or unsubstituted monovalent aromatic radical having a single ring (e.g., benzene) or two condensed rings (e.g., naphthyl). This term includes heteroaryl groups, which are aromatic ring groups having one or more nitrogen, oxygen, or sulfur atoms in the ring, such as furyl, pyrrole, pyridyl, and indole. By "substituted" is meant that one or more ring hydrogens in the aryl group is replaced with a halide such as fluorine, chlorine, or bromine; with a lower alkyl group containing one or two carbon atoms; nitro, amino, methylamino, dimethylamino, methoxy, halomethoxy, halomethyl, or haloethyl.

An "aliphatic disulfide" linkage intends a linkage of the form R'—S—S—R", where R' and R" are linear or branched alkyl chains that may be further substituted.

The following abbreviations are used herein: PEG, poly (ethylene glycol); mPEG, methoxy-PEG; DTB, dithiobenzyl; MeDTB, methyl-dithiobenzyl; EtDTB, ethyl-dithiobenzyl; DSPE, distearoyl phosphatidylethanolamine; DOPE, dioleoyl phosphatidylethanolamine; PHPC, partially hydrogenated phosphatidylcholine; MALDI-TOFMS, matrix-assisted laser desorption/ionization time-of-flight mass spectrometry.

II. The Compound of the Invention

In one aspect, the invention comprises a compound of the form:

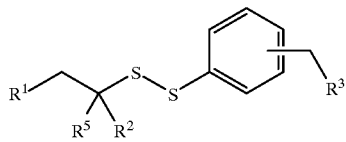

wherein $R^1$ comprises a hydrophilic polymer including functional group suitable for covalently attaching the polymer to the dithiobenzyl moiety. $R^2$ and $R^5$ are independently selected to be H, an alkyl or an aryl, and, as will be seen, can be varied to tailor the rate of disulfide cleavage. For example, to achieve a faster rate of cleavage, $R^2$ and $R^5$ are hydrogen. A slower rate of cleavage is achieved by sterically hindering the disulfide by selecting an alkyl or aryl for one or both of $R^2$ and $R^5$. $R^3$ comprises a linking moiety joined to $R^4$, which comprises an amine-containing ligand. The linking moiety in preferred embodiments is O(C=O), S(C=O) or O(C=O). The amine-containing ligand $R^4$ can be a primary or a secondary amine and can be selected from any number of substrates, including, but not limited to lipids, drugs, polypeptides, viruses, surfaces of biomaterials and aminoglycosides. In preferred embodiments, $R^4$ is a primary or secondary amine-containing lipid, drug or polypeptide. In the compound of the invention, the orientation of the group $CH_2$—$R^3$ can be either ortho or para.

FIG. 1A shows the structure of an exemplary compound in accord with the invention, where $R^1$ is the hydrophilic polymer methoxy-polyetheylene glycol, mPEG=$CH_3O$ $(CH_2CH_2O)_n$ where n is from about 10 to about 2300, which corresponds to molecular weights of about 440 Daltons to about 100,000 Daltons. The molecular weight of the polymer depends to some extent on the selection of $R^3$. In embodiments where $R^3$ is an amine-containing lipid for use in a liposome a preferred range of PEG molecular weight is from about 750 to about 10,000 Daltons, more preferably from about 2,000 to about 5,000 Daltons. The mPEG in this embodiment includes a urethane linking moiety. In embodiments where $R^3$ is an amine-containing polypeptide a preferred range of PEG molecular weight is from about 2,000 to about 40,000 Daltons, more preferably from about 2,000 to about 20,000 Daltons. It will be appreciated that $R^1$ can be selected from a variety of hydrophilic polymers, and exemplar polymers are recited above. It will also be appreciated that for some ligands, such as polypeptides, the molecular weight of the polymer may depend on the number of polymer chains attached to the ligand, where a larger molecular weight polymer is often selected when the number of attached polymer chains is small.

With continuing reference to FIG. 1a, $R^2$ and $R^5$ in this exemplary compound are H, however either or both $R^2$ and $R^5$ can also be a straight chain or branched alkyl or an aryl group. In a preferred embodiment, $R^5$ is H and $R^2$ is an alkyl, and several examples are given below. In the compound shown in FIG. 1A, $R^3$ takes the general form of O(C=O)-($NH_2$-ligand), where the $NH_2$-ligand can be any amine-containing polypeptide, drug or lipid, and specific examples of each embodiment are given below. R3 can also be of the form O(C=S)-($NH_2$-ligand) or S(C=O)-($NH_2$-ligand).

Figure 1B:
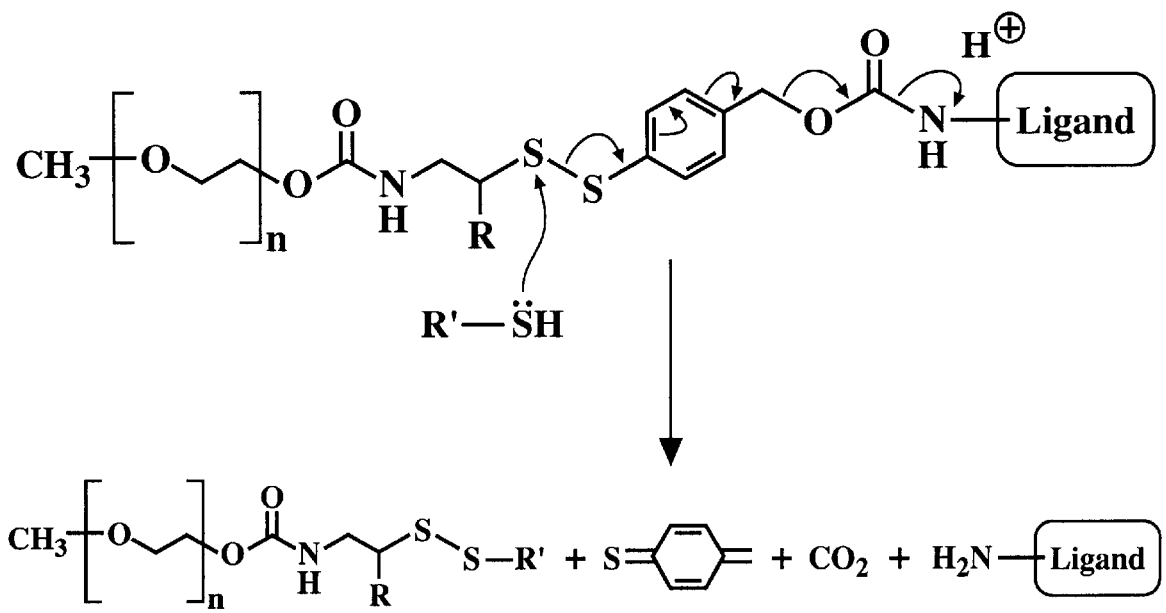
FIG. 1B shows the products after thiolytic cleavage of the compound in FIG. 1A.

FIG. 1B shows the mechanism of thiolytic cleavage of the mPEG-DTB-($NH_2$-ligand) compound of FIG. 1A. The ortho- or para-dithiobenzyl carbamate moiety is cleavable under mild thiolytic conditions, such as in the presence of cysteine or other naturally-occurring reducing agents. Upon cleavage, the amine-containing ligand is regenerated in its natural, unmodified form. Studies in support of the invention, described below, show that natural, physiologic conditions in vivo are sufficient to initiate and achieve cleavage of the DTB linkage. It will be appreciated that a reducing agent can also be administered to artificially induce thiolytic conditions sufficient for cleavage and decomposition of the compound.

As noted above, $R^3$ takes the general form of a linking moiety, such as O(C=O), S(C=O) or O(C=S) joined to an amine-containing ligand. In preferred embodiment, the amine-containing ligand comprises an amine-containing polypeptide, drug or lipid. Examples of these embodiments will now be described.

A. Amine-Containing Lipid

In one embodiment, the amine-containing ligand is an amine-containing lipid. Lipids as referred to herein intend water-insoluble molecules having at least one acyl chain containing at least about eight carbon atoms, more preferably an acyl chain containing between about 8–24 carbon atoms. A preferred lipid is a lipid having an amine-containing polar head group and an acyl chain. Exemplary lipids are phospholipids having a single acyl chain, such as stearoylamine, or two acyl chains. Preferred phospholipids with an amine-containing head group include phosphatidylethanolamine and phosphatidylserine. The lipid tail(s) can have between about 12 to about 24 carbon atoms and can be fully saturated or unsaturated. One preferred lipid is distearoylphosphatidylethanolamine (DSPE), however those of skill in the art will appreciate the wide variety of lipids that fall within this description. It will also be appreciated that the lipid can naturally include an amine group or can be derivatized to include an amine group. Other lipid moieties that do not have an acyl tail, such as cholesterolamine, are also suitable.

Figure 2:
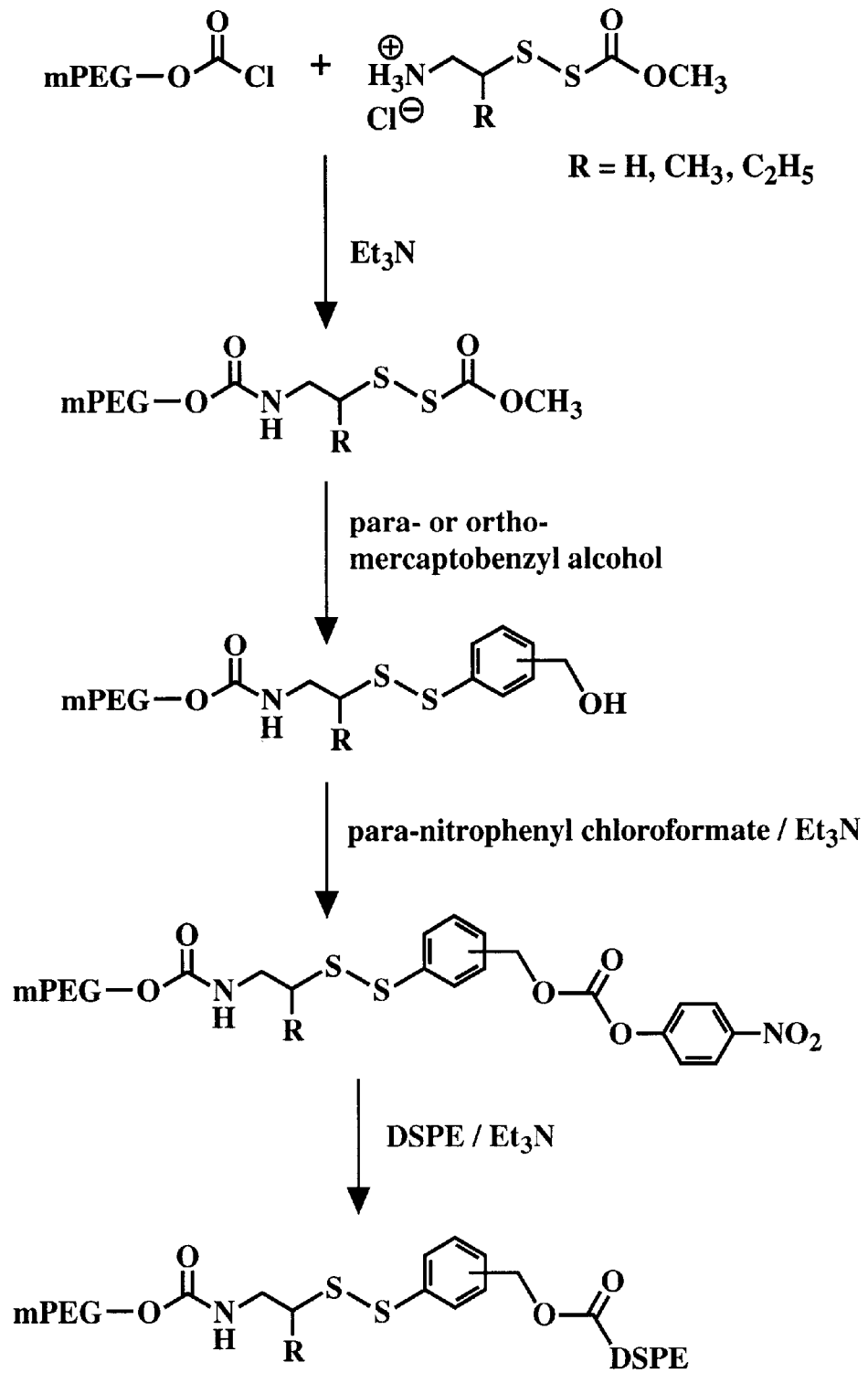
FIG. 2 illustrates a synthetic reaction scheme for synthesis of the mPEG-DTB-amine-lipid, where the amine-ligand is the lipid distearoylphosphatidylethanolamine (DSPE)

The synthesis of a polymer-DTB-lipid compound is schematically depicted in FIG. 2. mPEG derivatives (MW 2000 and 5000 Daltons) having a methoxycarbonyldithioalkyl end group were prepared by reacting 2-(methoxycarbonyldithio)ethaneamine with mPEG-chloroformate, which was readily prepared by phosgenation of dried mPEG-OH solution (Zalipsky, S., et al., *Biotechnol. Appl. Biochem.* 15:100–114 (1992).). The former compound was obtained through 2-aminoethanethiol hydrochloride reaction with an equivalent amount of methoxycarbonyl-sulfenyl chloride, according to published procedures (Brois, S. J., et al., *J. Amer. Chem. Soc.* 92:7629–7631 (1970); Koneko, T., et al., *Bioconjugate Chem.* 2:133–141 (1991)). Both the para and ortho isomers of mercaptobenzyl alcohol (Grice, R., et al., *J. Chem. Soc.* 1947–1954 (1963)) coupled cleanly with the resulting PEG-linked acyldisulfide, yielding mPEG bearing a dithio benzyl alcohol end group. Active carbonate introduction proceeded as with underivatized mPEG-OH, to give the para-nitrophenyl carbonate. Addition of DSPE in ethanolamine formed the desired mPEG-DTB-DSPE product. Both ortho- and para-DTB-lipid compounds were prepared and purified by silica gel chromatography and characterized by NMR and MALDI-TOFMS, the details of which are given in Example 1.

Figure 3:
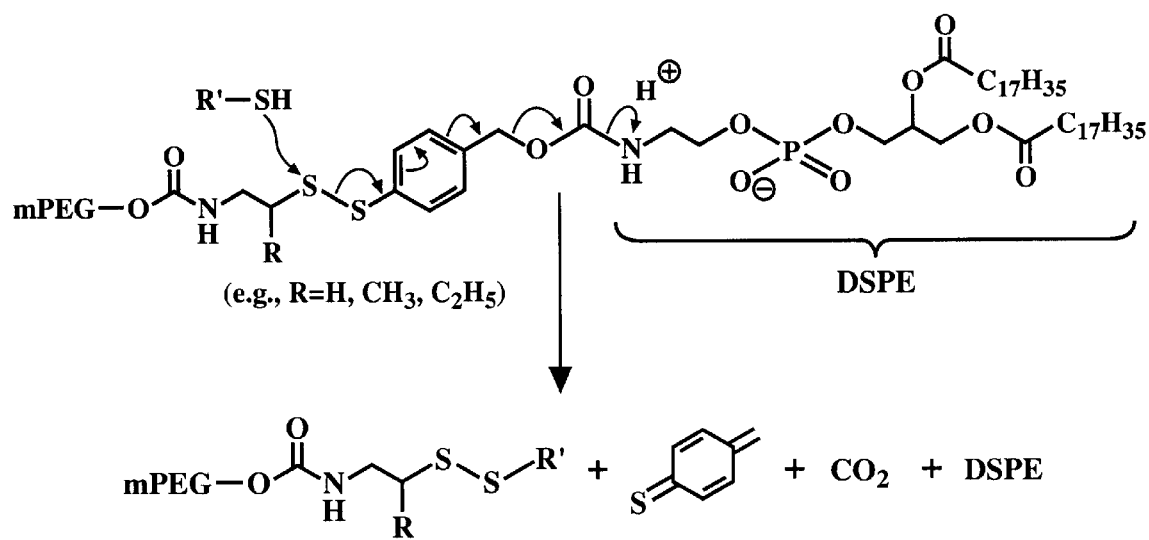
FIG. 3 illustrates the thiolytic cleavage mechanism of a para-dithiobenzyl urethane (DTB)-linked mPEG-DSPE conjugate.

FIG. 3 shows the mechanism of thiolytic cleavage of the mPEG-DTB-DSPE conjugate. Upon cleavage, the phosphatidylethanolamine lipid is regenerated in its natural, unmodified form.

Figure 4A:
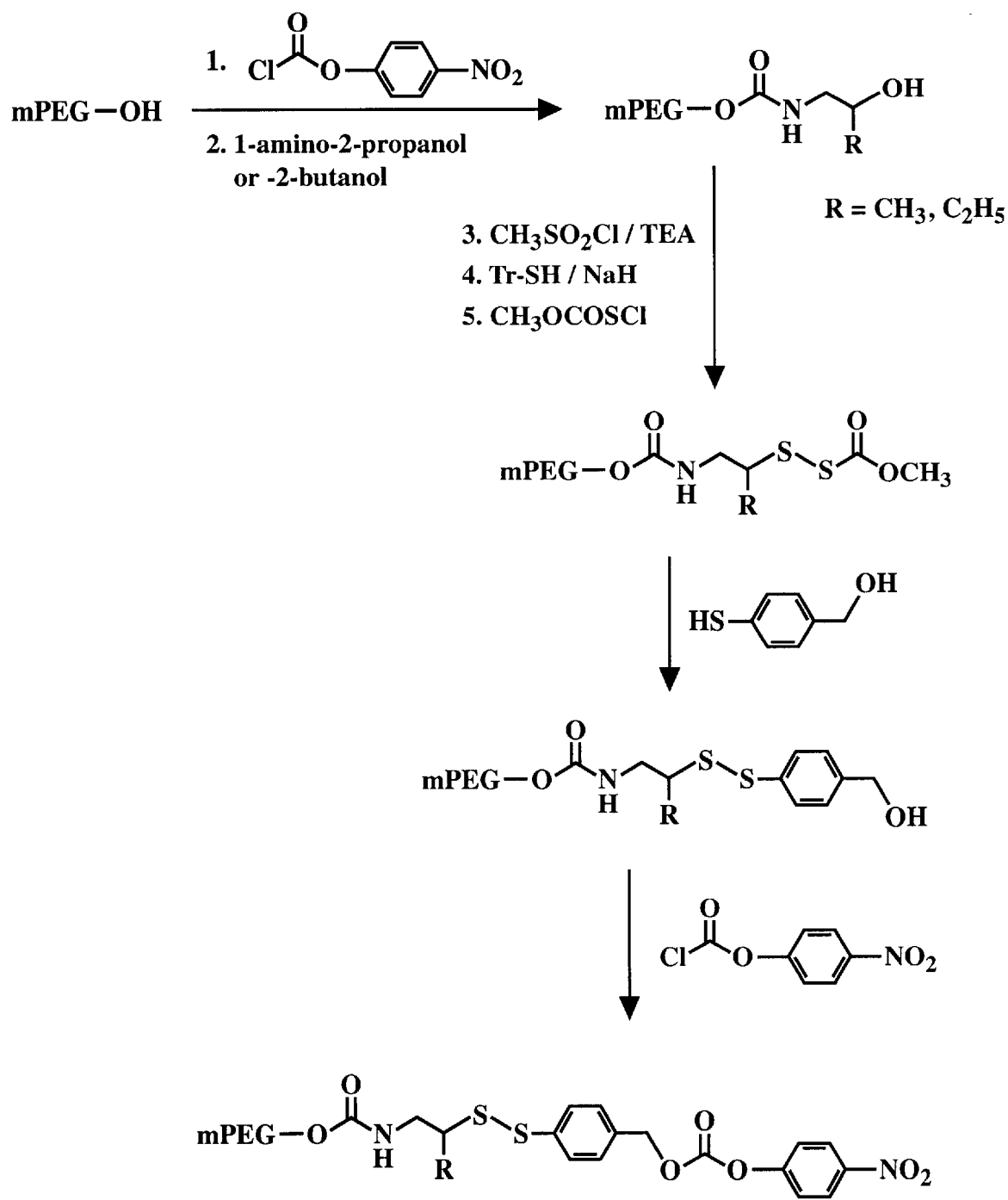
FIGS. 4A-4B show a synthetic reaction scheme for preparation of an mPEG-DTB-DSPE compound in accord with the invention where the DTB linkage is sterically hindered by an alkyl group.
Figure 4B:
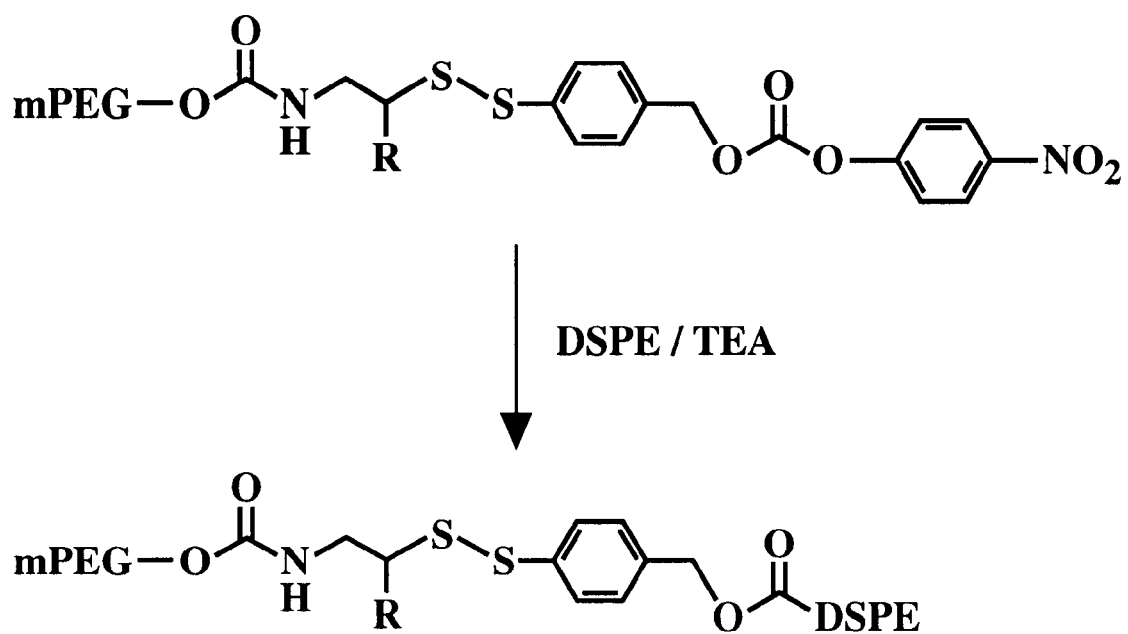

FIGS. 4A–4B show a reaction scheme for synthesis of mPEG-DTB-DSPE conjugates having an alkyl group adjacent the disulfide linkage, e.g., a more hindered disulfide linkage. As described more fully in Example 2A, mPEG-OH in dichloromethane was reacted with p-nitrophenylchloroformate in the presence of triethylamine (TEA) to form mPEG-nitrophenyl carbonate. An amino alcohol, such as 1-amino-2-propanol or 1-amino-2-butanol, in dimethylformamide (DMF) was reacted with the mPEG-nitrophenyl carbonate in the presence of TEA to form a secondary alcohol attached to PEG. The secondary alcohol was then converted to the desired mPEG-DTB-DSPE compound as illustrated in FIG. 4A and detailed in Example 2A.

In this reaction scheme, mPEG-methyl-dithiobenzyl-nitrophenyl chloroformate was reacted with DSPE to form the desired compound. The nitrophenyl chloroformate moiety in the mPEG-methyl-dithiobenzyl-nitrophenyl chloroformate compound acts as a leaving group to yield the desired product upon reaction with a selected lipid. The invention contemplates, in another aspect, a composition that comprises a compound produced by reaction with a compound such as mPEG-methyl-dithiobenzyl-$R^3$, where $R^3$ represents a leaving group joined through a linking moiety to the benzene ring. The leaving group is displaced upon reaction with an amine-containing ligand, such as DSPE, a polypeptide or an amine-containing drug. The leaving group is selected according to the reactivity of the amine in the ligand, and is preferably derived from various acidic alcohols that have a hydroxy- or oxy-containing leaving group. These include chloride, p-nitrophenol, o-nitrophenol, N-hydroxytetrahydrophthalimide, N-hydroxysuccinimide, N-hydroxyglutarimide, N-hydroxynorbornene-2,3-dicarboxyimide, 1-hydroxybenzotriazole, 3-hydroxypyridine, 4-hydroxypyridine, 2-hydroxypyridine, 1-hydroxy-6-trifluoromethylbenzotriazole, immidazole, triazole, N-methyl-imidazole, pentafluorophenol, trifluorophenol and trichlorophenol.

Example 2B describes preparation of an mPEG-EtDTB-lipid conjugate where the disulfide linkage is hindered by an ethyl moiety.

Figure 5:
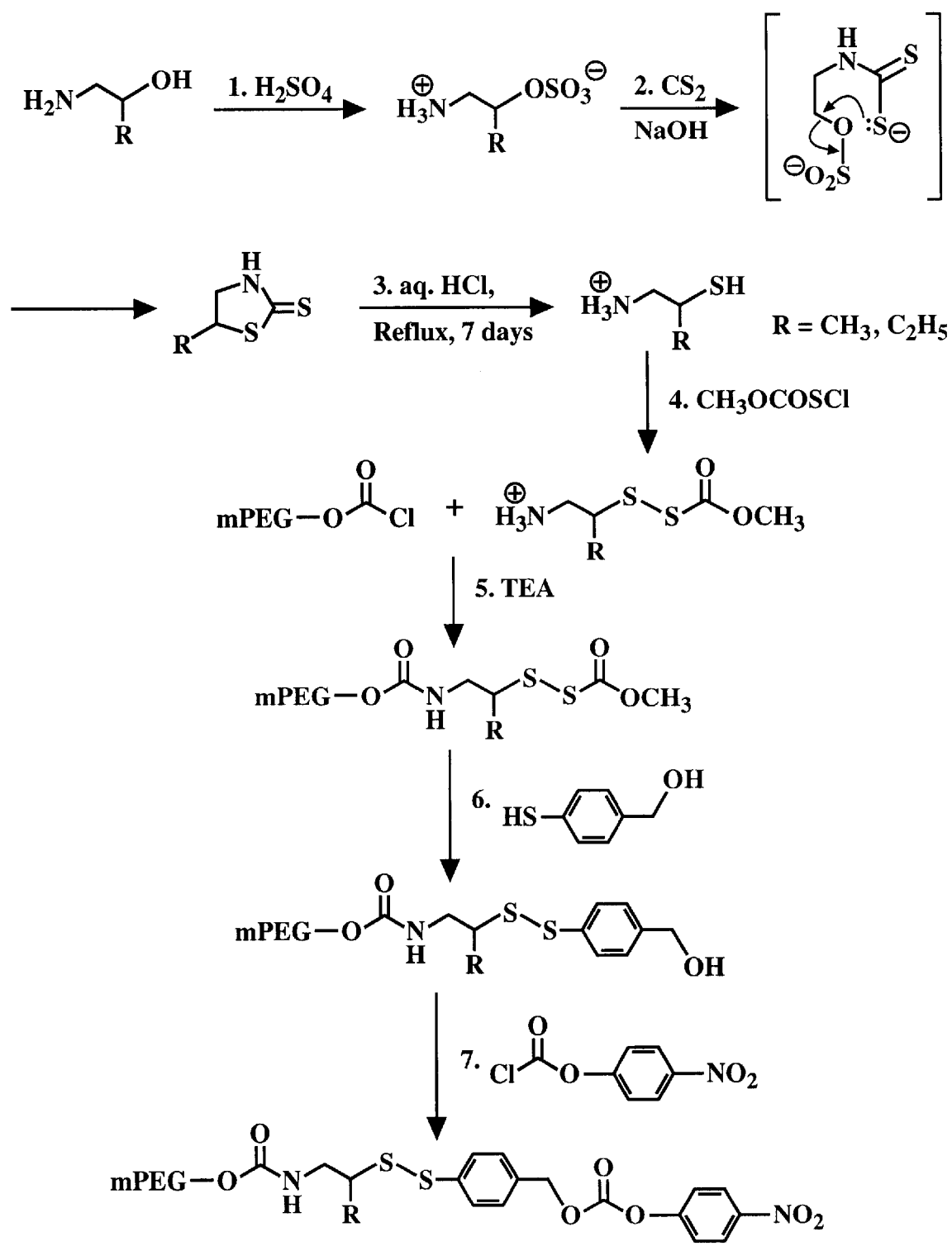
FIG. 5 shows another synthetic reaction scheme for preparation of an mPEG-DTB-ligand compound in accord with the invention.

FIG. 5 shows another synthetic reaction scheme for preparation of an mPEG-DTB-ligand compound in accord with the invention. The details of the reaction procedure are given in Examples 3A–3B. Briefly, cold 1-amino-2-propanol was reacted with sulfuric acid to form 2-amino-1-methylethyl hydrogen sulfate. This product was reacted with carbon disulfide and sodium hydroxide in aqueous ethanol to yield 5-methylthiazolidine-2-thione. An aqueous solution of hydrochloric acid was added to the 5-methylthiazolidine-2-thione and heated. After refluxing for one week, the product, 1-mercapto(methyl)ethyl ammonium chloride, was crystallized and recovered. This product was reacted with methoxy carbonylsulfenyl chloride to yield 2-(methoxycarbonyldithio)ethaneamine. Reaction of the 2-(methoxycarbonyldithio)ethaneamine with mPEG-chloroformate using the procedure described above with respect to FIG. 2 yields the desired mPEG-DTB-nitrophenyl compound suitable for reaction with a selected amine-containing ligand to form a compound in accord with the invention.

Example 3B describes the reaction for synthesis of mPEG-(ethyl)DTB-nitrophenyl.

Figure 6A:
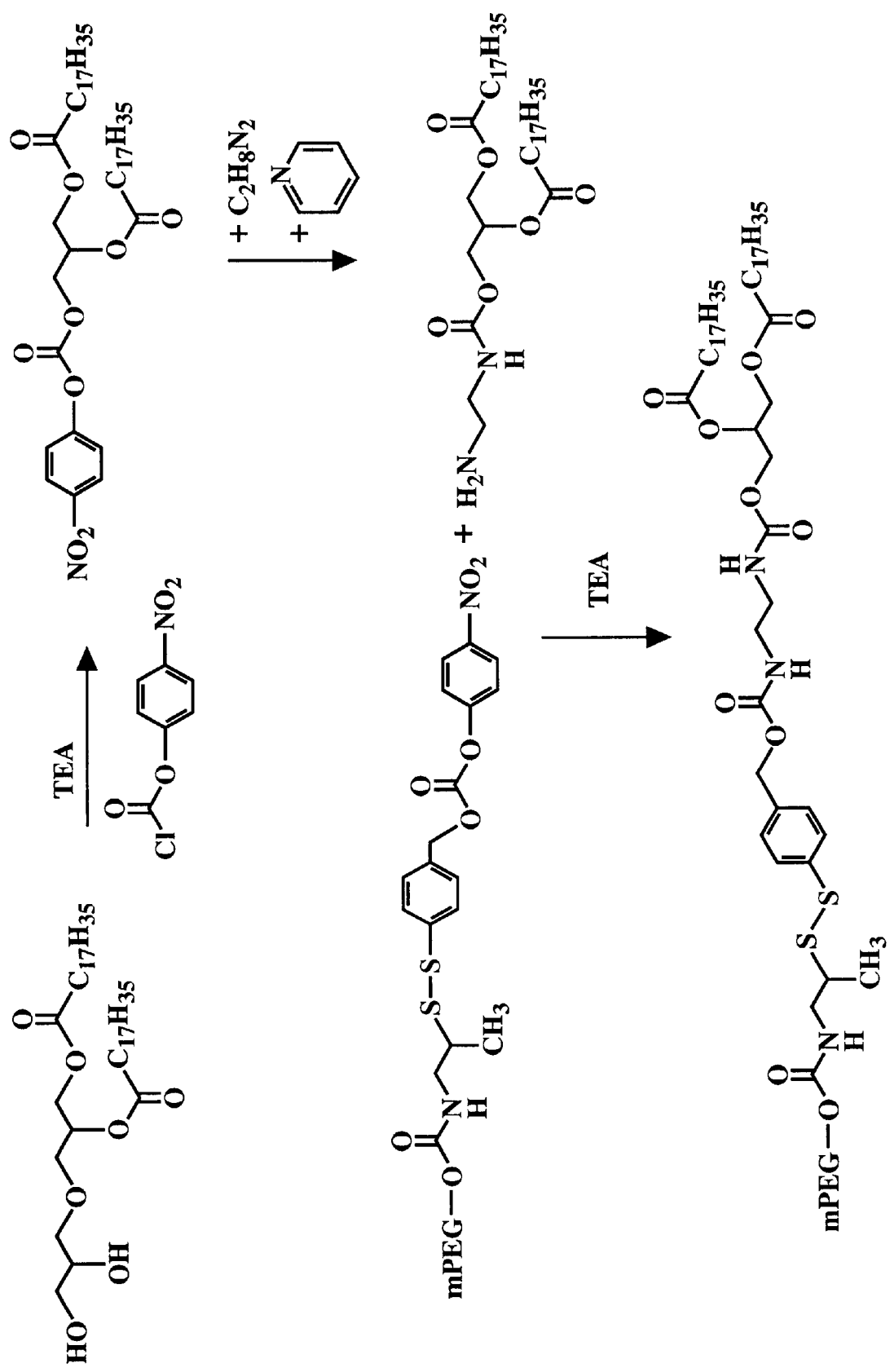
FIG. 6A is a synthetic reaction scheme for synthesis of an mPEG-DTB-lipid which upon thiolytic cleavage yields a cationic lipid.
Figure 6B:
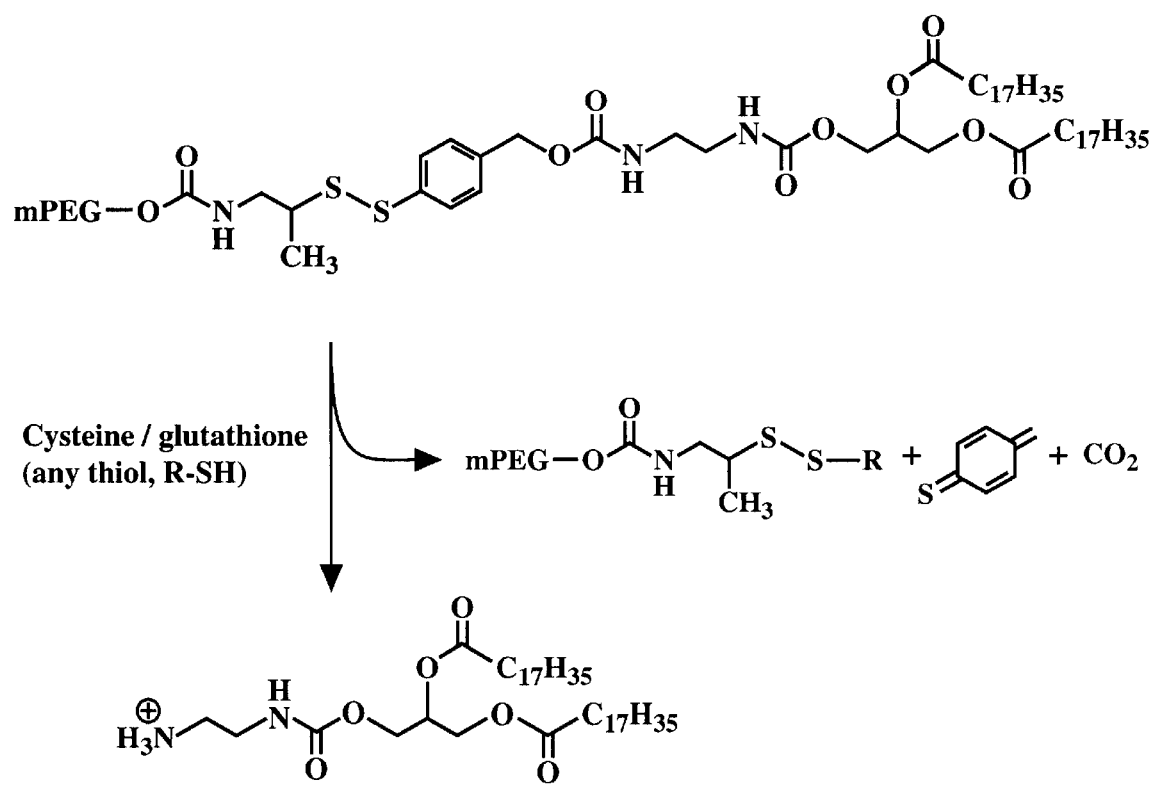
FIG. 6B shows the products after thiolytic cleavage of the compound in FIG. 6A.

FIG. 6A shows a reaction scheme for preparation of another mPEG-DTB-lipid compound in accord with the invention. The reaction details are provided in Example 4. The lipid 1,2-distearoyl-sn-glycerol is activated for reaction with mPEG-DTB-nitropheynl, prepared as described in FIG. 4A or FIG. 5. The resulting mPEG-DTB-lipid differs from the compounds described above in the absence of a phosphate head group. The mPEG-DTB-lipid of FIG. 6A is neutral prior to cleavage. As shown in FIG. 6B, upon thiolytic reduction of the disulfide bond, the compound decomposes to yield a cationic lipid. The positively-charged lipid provides for electrostatic interaction in vivo and commensurate advantages in in vivo targeting.

In the reaction schemes described above, $R^5$ of the claimed compound is H. However, in other embodiments $R^5$ is an alkyl or an aryl moiety. In this approach, for example where $R^2$ and $R^5$ are both $CH_3$ moieties, an α,β-unsaturated acyl chloride (R'R"C=CHCOCl, where R' is, for example $CH_3$ and R" is $CH_3$, however any alkyl or aryl is contemplated) is reacted with an amine-terminated PEG to give the corresponding N-PEG-substituted α,β-unsaturated amide. This compound is reacted with thiolacetic acid, giving the corresponding N-PEG-substituted β-(acetylthio) amide via conjugate addition to the C=C bond. The acetylthio group (—SCOCH$_3$) is hydrolyzed to a thiol group (—SH), which is then reacted with methyl (chlorosulfenyl) formate (ClSCOOCH$_3$), generating a methoxycarbonyl diothio group (—SSCOOCH$_3$); this intermediate is then reacted with p-mercapto benzyl alcohol to give the N-PEG-substituted β-(dithiobenzyl alcohol) amide (having the structure PEG-NH—CO—CH$_2$CR'R"-SS-p-phenyl-CH$_2$OH). The benzyl alcohol moiety is then reacted with nitrophenyl chloroformate to give the nitrophenyl carbonate leaving group, as above.

1. In vitro Cleavage of mPEG-DTB-DSPE Compound

Figure 7A:
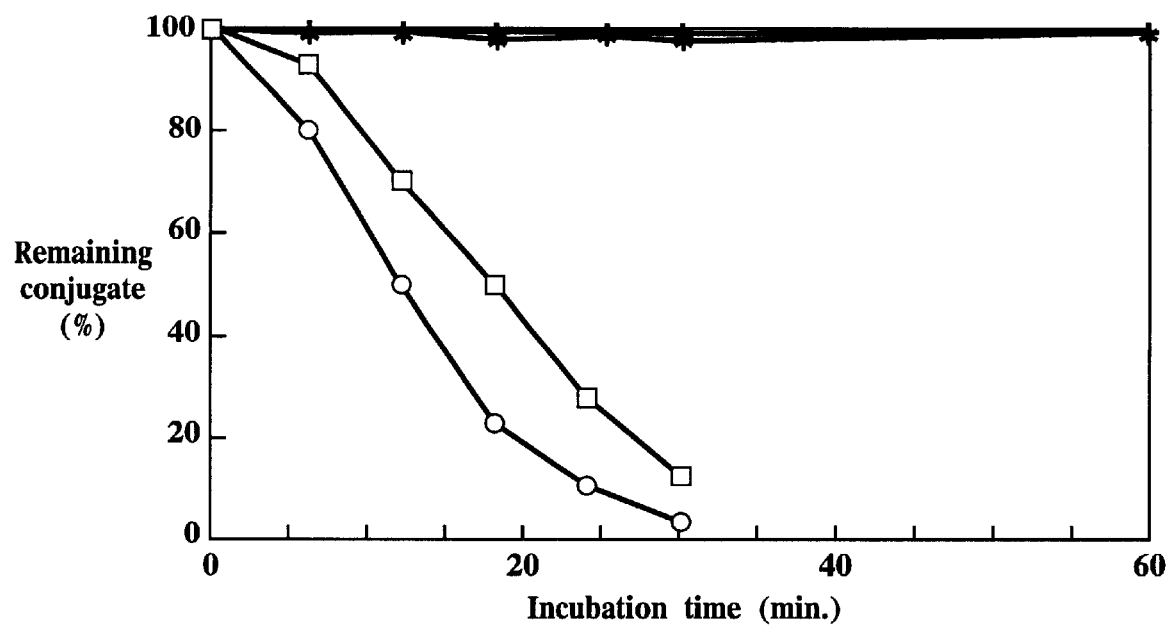
FIG. 7A shows the rate of cleavage of ortho-mPEG-DTB-DSPE and para-mPEG-DTB-DSPE conjugates in solution to form micelles in buffer alone (ortho-conjugate (*); para-conjugate (+)) and in the presence of 150 $\mu$M cysteine (ortho-conjugate (open circles); para-conjugate (open squares)

The in vitro rate of cleavage of ortho-mPEG-DTB-DSPE and para-mPEG-DTB-DSPE (prepared as described in Example 1) was studied by preparing micellar solutions of the compounds in a buffered aqueous solution (pH 7.2). Thiolytic cleavage of the compounds was monitored in the presence and absence of 150 μM cysteine by analyzing for disappearance of the compounds by HPLC, as described in Example 5. The results are illustrated in FIG. 7A where the ortho- and para-compounds in the absence of cysteine (* symbols and + symbols, respectively) show no cleavage and are stable under these conditions in the absence of cysteine. The ortho- and para-compounds, represented by the open circles and the open squares, respectively, in the presence of 150 μM cysteine cleave as shown in FIG. 7A. The ortho-compound exhibited a slightly faster rate of decomposition than its para counterpart ($T_{1/2}$ ≈12 minutes vs. ≈18 minutes).

2. Liposome Compositions Comprising an mPEG-DTB-lipid Compound a. In vitro Characterization In one embodiment, the mPEG-DTB-lipid compound is formulated into liposomes. Liposomes are closed lipid vesicles used for a variety of therapeutic purposes, and in particular, for carrying therapeutic agents to a target region or cell by systemic administration of liposomes. In particular, liposomes having a surface coating of hydrophilic polymer chains, such as polyethylene glycol (PEG), are desirable as drug carries, since these liposomes offer an extended blood circulation lifetime over liposomes lacking the polymer coating. The polymer chains in the polymer coating shield the liposomes and form a "stiff brush" of water solvated polymer chains about the liposomes. Thus, the polymer acts as a barrier to blood proteins, preventing binding of the protein and recognition of the liposomes for uptake and removal by macrophages and other cells of the reticuloendothelial system.

Typically, liposomes having a surface coating of polymer chains are prepared by including in the lipid mixture between about 1 to about 20 mole percent of the lipid derivatized with the polymer. The actual amount of polymer derivatized lipid can be higher or lower depending on the molecular weight of the polymer. In the present invention, liposomes are prepared by adding between about 1 to about 20 mole percent of the polymer-DTB-lipid conjugate to other liposome lipid bilayer components. As will be demonstrated in the studies described below, liposomes containing the polymer-DTB-lipid conjugate of the invention have a blood circulation lifetime the is longer than liposomes containing a polymer-lipid conjugate where the polymer and lipid are joined by a cleavable aliphatic disulfide bond.

Figure 7B:
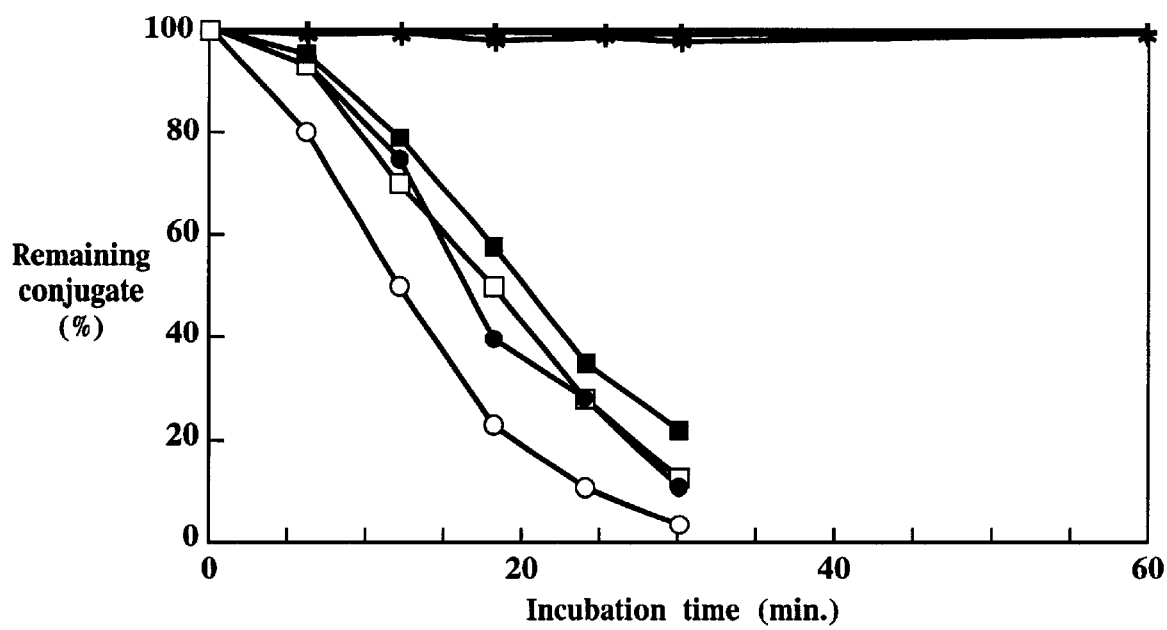
FIG. 7B shows the rate of cleavage of micellar mPEG-DTB-DSPE conjugates as described in FIG. 7A and of ortho-mPEG-DTB-DSPE (solid circles) and para-mPEG-DTB-DSPE (solid squares) conjugates formulated in liposomes and incubated in the presence of 150 $\mu$M cysteine.

In studies performed in support of the invention, liposomes comprised of the vesicle-forming lipid partially hydrogenated phosphatidyl choline along with cholesterol and the ortho-mPEG-DTB-DSPE or the para-mPEG-DTB-DSPE compound were prepared as described in Example 6. Cysteine-mediated cleavage of the mPEG-DTB-DSPE compounds was monitored in the presence and absence of 150 $\mu$M cysteine in an aqueous buffer. The results are shown in FIG. 7B, which includes the data of FIG. 7A for comparison. In FIG. 7B, the ortho- and para-compounds in micellar form in the absence of cysteine (* symbols and + symbols, respectively) show no cleavage, which indicates stability of the conjugate in the absence of thiols. The open circles and the open squares correspond to the ortho- and para-compounds, respectively, in micellar form in the presence of cysteine, as discussed above with respect to FIG. 7A. The solid circles and the solid squares correspond to the ortho- and para-compounds, respectively, in liposomal form in the presence of cysteine.

The data in FIG. 7B shows that both the ortho and para compound were slightly more resistant to thiolytic cleavage when incorporated into liposomes. Examination of the thiolysis reaction products by TLC (silica gel G, chloroform/ methanol/ water 90:18:2) (Dittmer, J. C., et al., *J. Lipid Res.* 5:126–127 (1964)) showed DSPE as the sole lipid component and another spot corresponding to a thiol-bearing, lipid-free mPEG derivative.

In another study performed in support of the invention, liposomes were prepared from the lipid dioleoyl phosphatidylethanolamine (DOPE) and either the ortho-mPEG-DTB-DSPE or the para-mPEG-DTB-DSPE compound were prepared. DOPE is a hexagonal phase lipid which alone does not form lipid vesicles. However, liposomes will form when DOPE is combined with a few mole percent of the mPEG-DTB-DSPE compound. Cleavage of the mPEG-DTB-DSPE compound triggers decomposition of the liposomes and release of liposomally-entrapped contents. Thus, the content release characteristics of such liposomes provides for a convenient quantitative evaluation of cleavable PEG-bearing liposomes.

Liposomes comprised of DOPE and the ortho- or para-mPEG-DTB-DSPE compound were prepared as described in Example 7A with entrapped fluorophores, p-xylene-bis-pyridinium bromide and trisodium 8-hydroxypyrenetrisulfonate. Release of the fluorophores from liposomes incubated in the presence of cysteine at various concentrations was monitored as described in Example 7B.

Figure 8A:
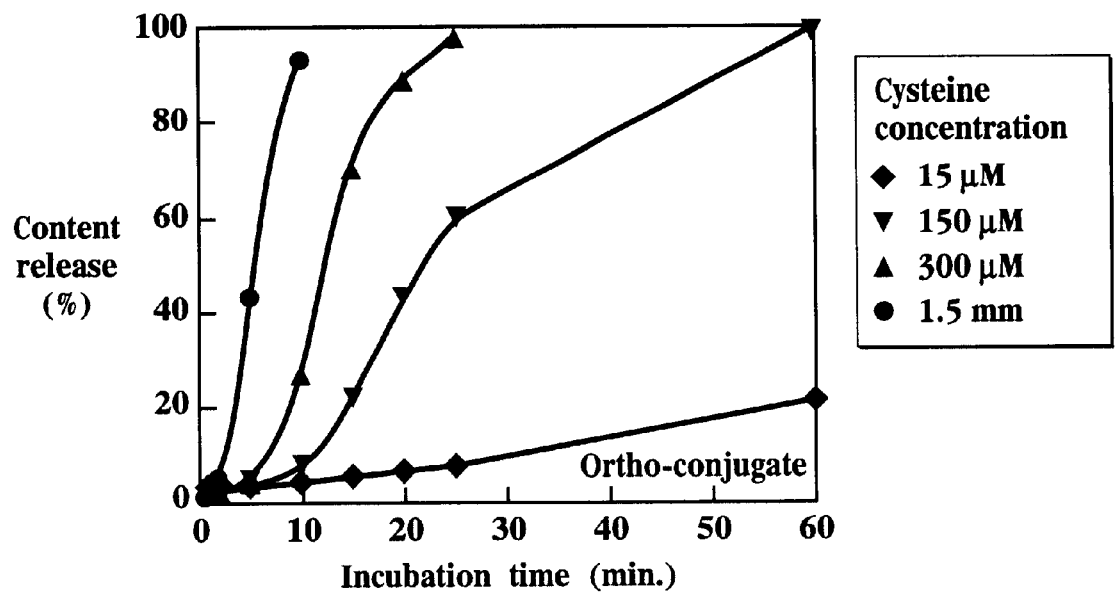
FIGS. 8A–8B show percentage of content release of entrapped fluorophore from liposomes comprised of DOPE:ortho-mPEG-DTB-DSPE (FIG. 8A) or of DOPE:para-mPEG-DTB-DSPE (FIG. 8B) incubated in the presence of cysteine at the indicated concentrations.
Figure 8B:
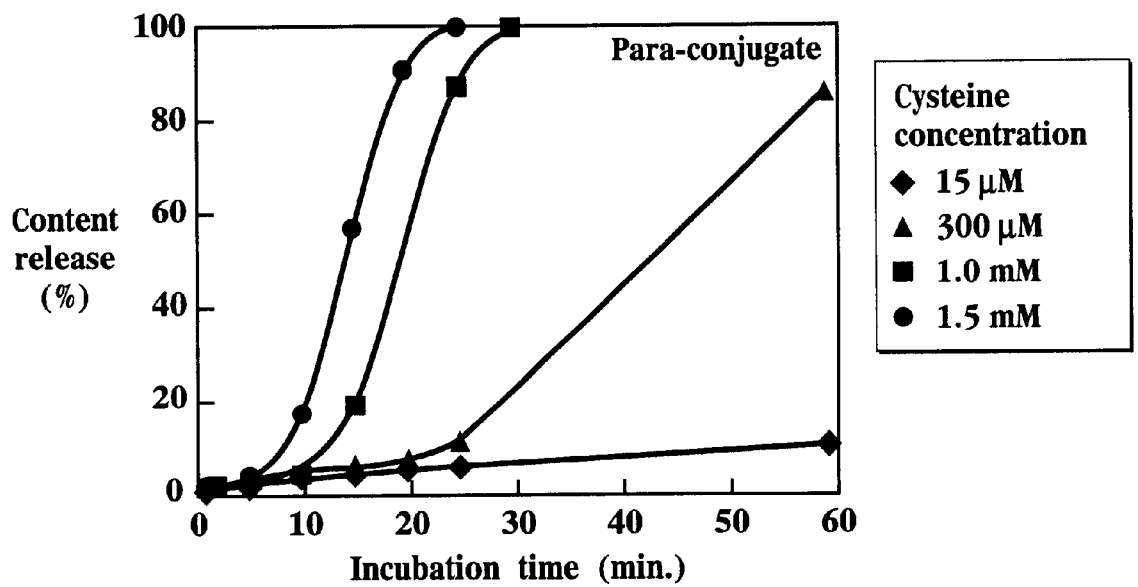

Results for liposomes comprising the ortho-compound are shown in FIG. 8A, where percentage of content release of entrapped fluorophore from liposomes incubated in the presence of cysteine at concentrations of 15 $\mu$M (solid diamonds), 150 $\mu$M (solid inverted triangles), 300 mM (solid triangles) and 1.5 $\mu$M (solid circles) are shown. FIG. 8B is a similar plot for liposomes comprising the para-compound, where the liposomes are incubated in cysteine at concentrations of 15 $\mu$M (solid diamonds), 300 $\mu$M (solid triangles), 1 $\mu$M (solid squares) and 1.5 mM (solid circles).

FIGS. 8A–8B show that both the ortho- and para-compounds when incorporated into liposome are cleaved, as evidenced by release of the entrapped dye, at a rate dependent on the concentration of cysteine. Control studies with non-cleavable mPEG-DSPE containing liposomes produced no content release (results not shown here). These results also suggest that the ortho conjugate is somewhat more susceptible to thiolytic cleavage. For example, 300 $\mu$M cysteine liberates most of the contents of DOPE liposomes within 20 minutes. Under the same conditions, only a fraction of liposomes having para-mPEG-DTB-DSPE decomposed. Similarly, after incubation for 20 minutes at 150 $\mu$M cysteine, half of the entrapped contents was released for the ortho-containing liposomes, while only approximately 10% of the contents were release in liposomes containing the para-compound. Both ortho and para compounds have half-lives of less than 20 minutes at a cysteine level of 150 $\mu$M (see data in FIG. 7B). This suggests that more than half of the original three mole percent of the mPEG-DTB-lipid must be cleaved to observe content release from the liposomes.

Decomposition of the mPEG-DTB-DSPE/DOPE liposomes in 15 $\mu$M cysteine, the average plasma concentration in both humans and rodents (Lash, L.H., et al., *Arch. Biochem. Biophys.* 240:583–592 (1985)), was minimal in the time frame of these experiments (60 minutes). This suggests that the mPEG-DTB-lipid compounds should have sufficiently long lifetimes in plasma to allow the PEG-grafted vesicles to distribute systemically in vivo, or to accumulate in a specific site either passively or through ligand-mediated targeting. Local or short term increase in cysteine concentration can potentially be achieved by its intravenous or intra-arterial administration. The results shown in FIGS. 8A–8B also suggest that a prolonged exposure to the natural plasma cysteine concentration ($\approx$15 $\mu$M) would be sufficient to decompose most of these compounds. These suggestions were studied in in vivo experiments, described below.

In another study performed in support of the invention, liposomes comprised of DOPE and three different mPEG-DTB-lipid compounds were prepared. The liposomes were prepared as described in Example 7 and included and entrapped fluorophore. The three mPEG-DTB-lipid compounds were mPEG-DTB-DSPE as shown in FIG. 1A; mPEG-MeDTB-DSPE as shown in FIG. 4E, where R is CH$_3$, and mPEG-MeDTB-distearoyl-glycerol, as shown in FIG. 6A. The liposomes were comprised of 97 mole percent DOPE and 3 mole percent of one of the mPEG-DTB-lipid compounds. Cysteine-mediated rate of cleavage of the compounds was determined by monitoring the release of entrapped fluorophore as a function of time in the presence of various cysteine concentrations. The results are shown in FIGS. 9A–9C where the percent release of entrapped fluorophore is normalized for the release rate from liposomes incubated in buffer alone.

Figure 9A:
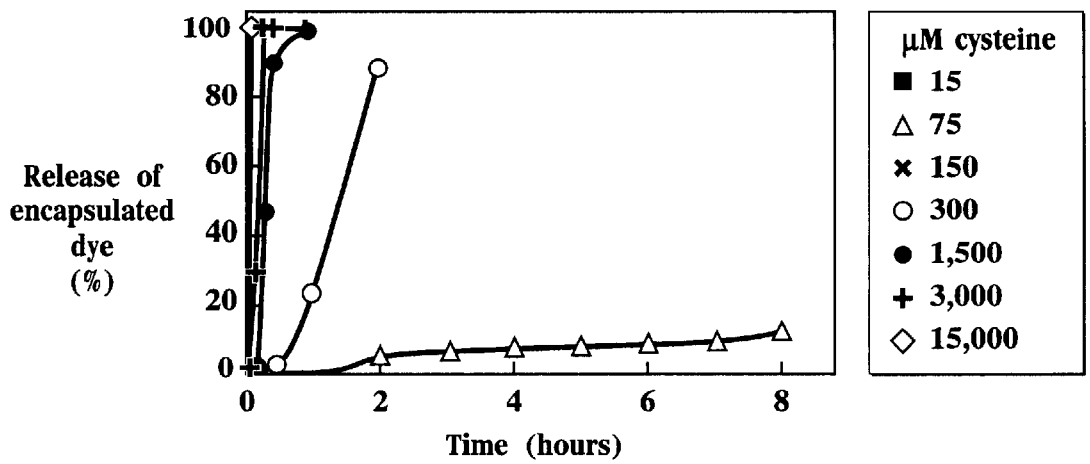
FIG. 9A shows normalized percent release of entrapped fluorophore as a function of time for liposomes comprised of DOPE and para-mPEG-DTB-DSPE. The percent release of entrapped fluorophore is normalized with respect to percent release of fluorophore from liposomes incubated in the absence of cysteine. The release rate from liposomes incubated in the presence of cysteine at concentrations of 15 µM (solid squares), 75 µM (open triangles), 150 µM (X symbols), 300 µM (open circles), 1500 µM (solid circles), 3000 µM (+ symbols), and 15000 µM (open diamonds) is shown.

FIG. 9A shows the percent release of entrapped fluorophore as a function of time for liposomes comprised of DOPE and para-mPEG-DTB-DSPE (compound of FIG. 1A). The release rate from liposomes containing the conjugate and incubated in the presence of cysteine at concentrations of 15 $\mu$M (solid squares), 75 $\mu$M (open triangles), 150 $\mu$M (X symbols), 300 $\mu$M (open circles), 1500 $\mu$M (solid circles), 3000 $\mu$M (+ symbols), and 15000 $\mu$M (open diamonds) is shown.

Figure 9B:
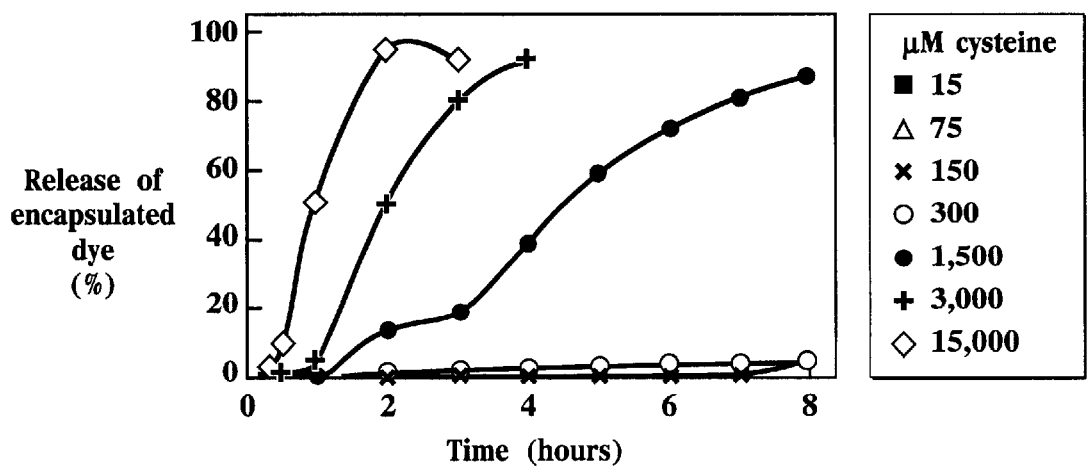
FIG. 9B shows normalized percent release of entrapped fluorophore as a function of time for liposomes comprised of DOPE and para-mPEG-MeDTB-DSPE. The percent release of entrapped fluorophore is normalized with respect to percent release of fluorophore from liposomes incubated in the absence of cysteine. The release rate for liposomes incubated in the presence of cysteine at concentrations of 15 µM (solid squares), 75 µM (open triangles), 150 µM (X symbols), 300 µM (open circles), 1500 µM (solid circles), 3000 µM (+ symbols), and 15000 µM (open diamonds) is shown.

FIG. 9B shows the percent release of entrapped fluorophore as a function of time for liposomes comprised of DOPE and para mPEG-MeDTB-DSPE (compound of FIG. 4B). The release rate of the fluorophore from liposomes incubated in the presence of cysteine at concentrations of 15 $\mu$M (solid squares), 75 $\mu$M (open triangles), 150 $\mu$M (X symbols), 300 $\mu$M (open circles), 1500 $\mu$M (solid circles), 3000 $\mu$M (+ symbols), and 15000 $\mu$M (open diamonds) is shown.

Figure 9C:
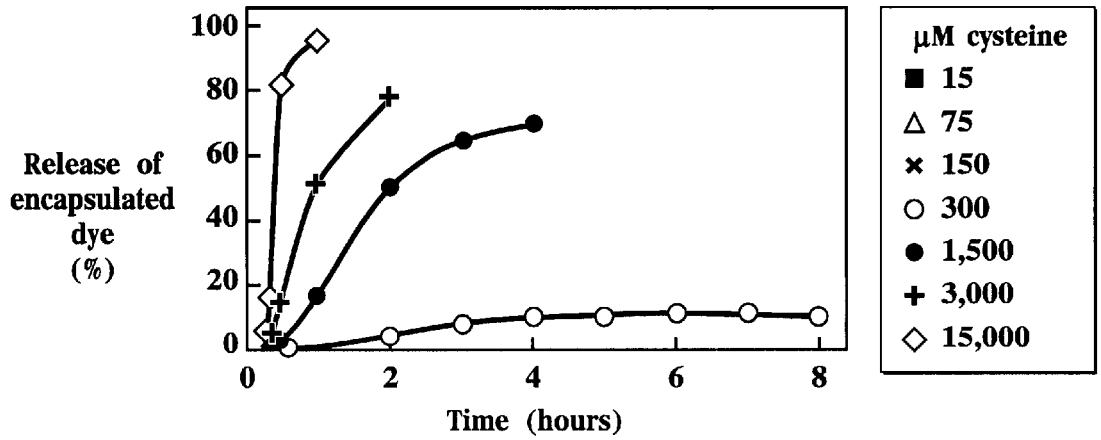
FIG. 9C shows normalized percent release of entrapped fluorophore as a function of time for liposomes comprised of DOPE and mPEG-meDTB-distearoyl-glycerol compound of FIG. 6A. The percent release of entrapped fluorophore is normalized with respect to percent release of fluorophore from liposomes incubated in the absence of cysteine. The release rate of dye upon cleavage of the compound from liposomes incubated in the presence of cysteine at concentrations of 15 µM (solid squares), 75 µM (open triangles), 150 µM (X symbols), 300 µM (open circles), 1500 µM (solid circles), 3,000 µM (+ symbols), and 15,000 µM (open diamonds) is shown.

FIG. 9C is a similar plot for liposomes formed with DOPE and mPEG-MeDTB-distearoyl glycerol (compound of FIG. 6A). The release rate of dye from liposomes incubated in the presence of cysteine at concentrations of 15 $\mu$M (solid squares), 75 $\mu$M (open triangles), 150 $\mu$M (X symbols), 300 $\mu$M (open circles), 1500 $\mu$M (solid circles), 3000 $\mu$M (+ symbols), and 15000 $\mu$M (open diamonds) is shown.

FIGS. 9A–9C show that the rate of mPEG-MeDTB-lipid cleavage is cysteine-concentration dependent, with a slow rate of cleavage, as evidenced by release of entrapped fluorophore, at cysteine concentrations of 15–75 $\mu$M. In comparing the data in FIG. 9A with that in FIG. 9B, it is seen that the mPEG-MeDTB-DSPE compound (FIG. 9B) cleaves approximately 10 times more slowly than the mPEG-DTB-DSPE compound (FIG. 9A). Thus, the rate of cleavage can be tailored according to the P moiety (see FIG. 2) in the DTB linkage.

b. In vivo Characterization

The blood circulation lifetime of liposomes prepared as described in Example 8 and that include a polymer-DTB-lipid conjugate in accord with the invention was determined in mice. In$^{111}$ was entrapped in the liposomes and the liposomes were administered by intravenous injection. One group of test animals additionally received an injection of cysteine, the control group of animals additionally received an injection of saline. Blood samples were taken at various times and analyzed for the presence of liposomes, as evidenced by the presence of In$^{111}$.

Figure 10:
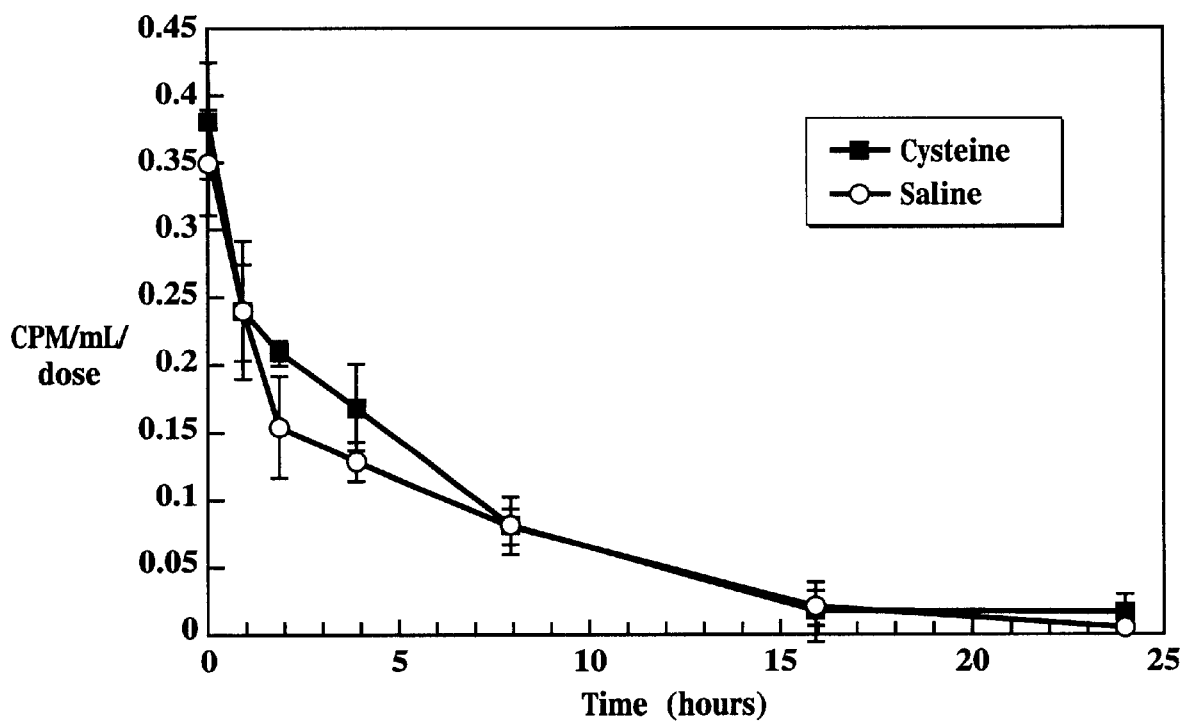
FIG. 10 is a plot showing the amount of liposomes, in counts per minute/mL of liposomes containing entrapped $In^{111}$, in blood samples taken from mice at various times after injection of liposomes comprised of PHPC:cholesterol:mPEG-DTB-DSPE (55:40:5 molar ratio). One group of animals received a 200 µL injection of 200 mM cysteine at time zero (solid squares). The control group was injection with saline at time zero (open circles)

FIG. 10 shows the results where the counts per minute (CPM) of In$^{111}$ is shown as a function of time following injection of the liposomes and saline (open circles) or 200 mM cysteine (solid squares). As seen, the cleavage of the mPEG-DTB-DSPE occurred upon exposure to the naturally-occurring physiologic conditions, as evidenced by the cleavage in the group of mice treated with saline after administration of the liposomes. Administration of an exogeneous reducing agent, cysteine, to the mice was effective to increase the rate of cleavage of the mPEG-DTB-lipid compound in the time frame from between about 2 hours to about 8 hours.

Importantly, cleavage of the polymer-DTB-lipid compound of the invention results in regeneration of the original lipid in unmodified form. This is desirable since unnatural, modified lipids can have undesirable in vivo effects. At the same time, the compound is stable when stored in the absence of reducing agents.

In other studies, not shown here, the blood circulation lifetime of liposomes containing the mPEG-DTB-lipid were compared to liposomes containing a polymer-lipid conjugate where the polymer and lipid are joined by a cleavable aliphatic disulfide bond. Aliphatic disulfide linkages are readily cleaved in vivo and the blood circulation lifetime of liposomes having polymer chains grafted to their surface by an aliphatic disulfide typically do not have the extended blood circulation lifetime observed for liposomes having stably linked polymer chains. The dithiolbenzyl linkage of the invention, and in particular the more hindered DTB linkages, are more stable in vivo and achieve a longer blood circulation lifetime than liposomes with polymer chains attached via an aliphatic disulfide linkage.

B. Amine-Containing Polypeptide

Figure 11A:
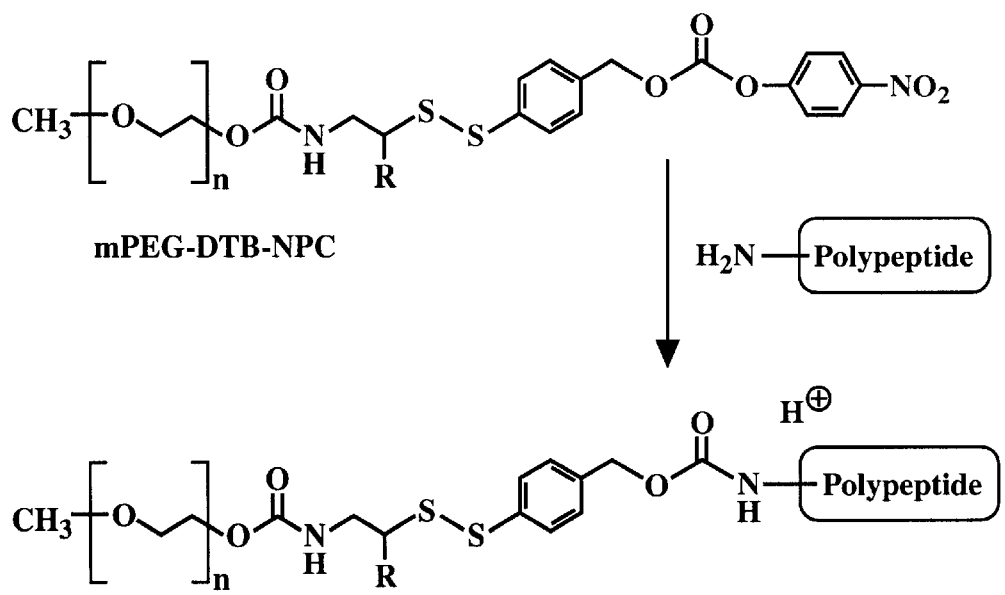
FIG. 11A shows a synthetic reaction scheme for synthesis of an mPEG-DTB-protein compound in accord with another embodiment of the invention.

In another embodiment, the invention includes a compound as described with respect to FIG. 1A, where the amine-containing ligand is a polypeptide. A synthetic reaction scheme showing preparation of a polymer-DTB-polypeptide is shown in FIG. 11A, with mPEG as the exemplary polymer. In general, a mPEG-DTB-leaving group compound is prepared according to one the synthetic routes described above in FIGS. 2, 4A and 5. The leaving group can be nitrophenyl carbonate or any one of the others described above. The mPEG-DTB-nitrophenyl carbonate compound is coupled to an amine moiety in a polypeptide by a urethane linkage. The R group adjacent the disulfide in the compound can be H, $CH_3$, $C_2H_5$ or the like and is selected according to the desired rate of disulfide cleavage.

Figure 11B:
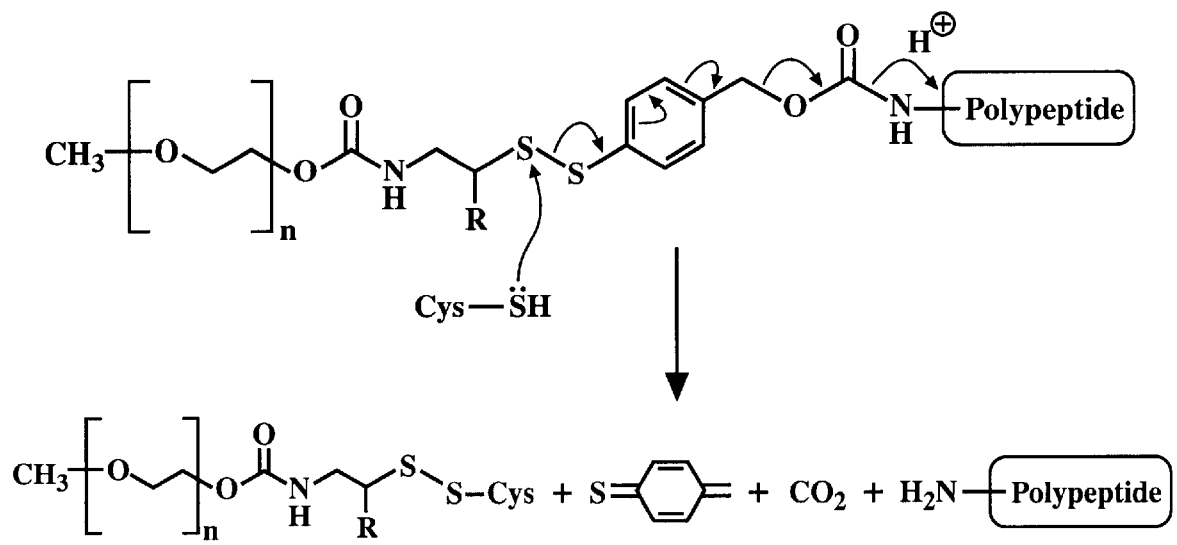
FIG. 11B shows the decomposition products after thiolytic cleavage of the compound in FIG. 11A.

FIG. 11B shows the decomposition products upon cysteine-mediated cleavage of the compound. As seen the native protein with no modification to the protein amine group is regenerated upon cleavage.

Attachment of polymer chains, such as PEG, to a polypeptide often diminishes the enzymatic or other biological activity, e.g., receptor binding, of the polypeptide. However, polymer modification of a polypeptide increases the blood circulation lifetime of the polypeptide. In the present invention, the polymer-modified polypeptide is administered to a subject. As the polymer-modified polypeptide circulates exposure to physiologic reducing conditions, such as blood cysteine and other in vivo thiols, initiates cleavage of the polymer chains from the polypeptide. As the polymer chains are released from the polypeptide, the biological activity of the polypeptide is gradually restored. In this way, the polypeptide initially has a sufficient blood circulation lifetime for biodistribution, and over time regains its full biological activity as the polymer chains are cleaved.

In a study performed in support of the invention, lysozyme was used as a model polypeptide and an mPEG-MeDTB-lysozyme conjugate was prepared by a synthetic route similar to those described above. Lysozyme was incubated with mPEG-MeDTB-nitrophenylcarbonate in 0.1 M borate, at pH 9 at a 2:1 ratio of nitrophenylcarbonate to amino group of lysozyme. After reactions times of 15 minutes and 3 hours, samples were characterized by SDS-PAGE. A comparative compound was prepared by reacting lysozyme under the same conditions for 60 minutes with a conjugate of mPEG-nitrophenyl carbonate, which will form a stable mPEG-lysozyme conjugate.

Figure 12:
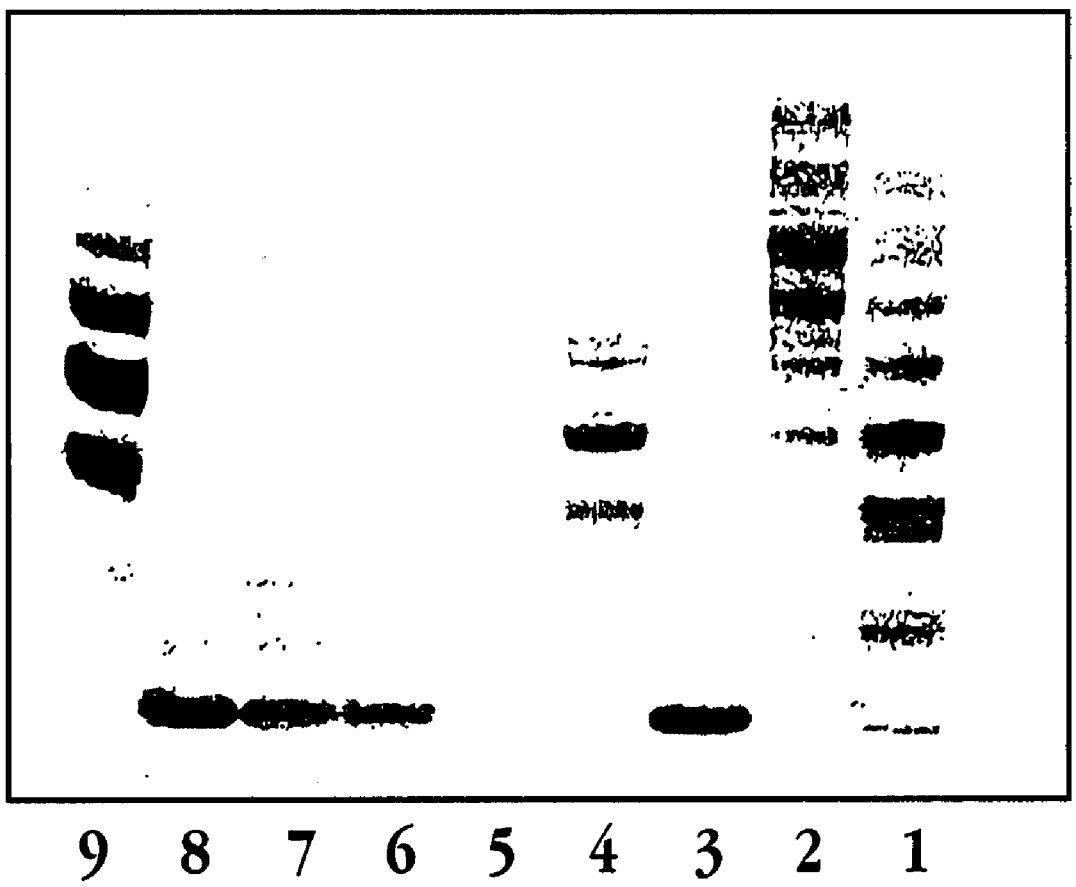
FIG. 12 is a rendering of a photograph of an sodium-dodecyl-sulfate polyacrylamide gel electrophoresis (SDS-PAGE) profile of lysozyme reacted for 15 minutes (Lane 1) or for 1 hour (Lane 2) with mPEG-MeDTB-nitrophyenylchloroformate to form a mPEG-MeDTB-lysozyme conjugate, native lysozyme (Lane 3), lysozyme reacted for 1 hour with mPEG-nitrophenylchloroformate (Lane 4), molecular weight markers (Lane 5), and the samples of Lanes 1–4 treated with 2% β-mercaptoethanol for 10 minutes at 70° C. (Lanes 6–9)

FIG. 12 shows a rendering of the SDS-PAGE gel. Lane 1 corresponds to the compound formed after 15 minutes reaction of lysozyme with mPEG-MeDTB-nitrophyenylcarbonate and Lane 2 represents the compound formed after a 1 hour reaction time of the same compounds. Lane 3 represents native lysozyme and Lane 4 corresponds to lysozyme reacted for 1 hour with mPEG-nitrophenylcarbonate. The molecular weight markers in Lane 5 are as follows, from the top down:

| Molecular Weight (kDaltons) | Marker |
|---|---|
| 1163 | β-galactosidase |
| 97.4 | phosphorylase b |
| 66.3 | bovine serum albumin |
| 55.4 | glutamic dehydrogenase |
| 36.5 | lactate dehydrogenase |
| 31 | carbonic anhydrase |
| 21.5 | trypsin inhibitor |
| 14.4 | lysozyme |

Comparison of Lane 1 and Lane 2 shows that the longer reaction time results in an increase in compound molecular weight, consistent with additional mPEG chains conjugated to the polypeptide at longer incubation time.

Lanes 6–9 of the SDS-PAGE profile correspond to the samples in Lanes 1–4 after treatment with 2% β-mercaptoethanol for 10 minutes at 70° C. The mPEG-MeDTB-lysozyme conjugate after exposure to a reducing agent decomposed to regenerate native lysozyme, as evidenced by the band in Lanes 6 and 7 at 14.4 kDa. In contrast, the stable mPEG-lysozme compound was not affected upon incubation with a reducing agent, as evidenced by the agreement in the profile in Lane 9 and Lane 4.

Also evident from the SDS-PAGE profile is that covalent attachment of mPEG-MeDTB to a protein forms a mixture of conjugates containing various mPEG-protein ratios. This ratio is dependent on the reaction time and conditions. This is clearly seen in viewing the bands in Lanes 1 and 2, where Lane 1 shows lysozyme derivatized with from about 1–6 PEG chains. In Lane 2, the longer reaction time yielded mPEG-MeDTB-lysozyme conjugates with a higher mPEG-protein ratio. All cleavable conjugates were readily cleaved to regenerate the native protein, as seen in the bands of Lanes 6 and 7.

It will be appreciated that any of the hydrophilic polymers described above are contemplated for use. The molecular weight of the polymer is selected depending on the polypeptide, the number of reactive amines on the polypeptide and the desired size of the polymer-modified compound.

Polypeptides contemplated for use are unlimited and can be naturally-occurring or recombinantly produced polypeptides. Small, human recombinant polypeptides are preferred, and polypeptides in the range of 10–30 KDa are preferred. Exemplary polypeptides include cytokines, such as tumor necrosis factor (TNF), interleukins and interferons, erythropoietin (EPO), granulocyte colony stimulating factor (GCSF), enzymes, and the like. Viral polypeptides are also contemplated, where the surface of a virus is modified to include one or more polymer chain linked via a DTB reversible linkage. Modification of a virus containing a gene for cell transfection would extend the circulation time of the virus and reduce its immunogenicity, thereby improving delivery of an exogeneous gene.

C. Amine-Containing Drug

In yet another embodiment of the invention, a compound of the form polymer-DTB-amine-containing drug is contemplated. The compound is of the structure described above, and in particular with respect to FIG. 1A where the amine-containing ligand in the figure is the amine-containing drug. Modification of therapeutic drugs with PEG is effective to improve the blood circulation lifetime of the drug and to reduce any immunogenicity.

A polymer-DTB-amine-containing drug is prepared according to any of the reaction schemes described above, with modifications as necessary to provide for the particular drug. A wide variety of therapeutic drugs have a reactive amine moiety, such as mitomycin C, bleomycin, doxorubicin and ciprofloxacin, and the invention contemplates any of these drugs with no limitation. It will be appreciated that the invention is also useful for drugs containing an alcohol or carboxyl moiety. In the case where the drug contains a hydroxyl or carboxyl moiety suitable for reaction, the polymer-DTB moiety can be linked to the drug via urethane, ester, ether, thioether or thioester linkages. In all of these embodiments, the polymer-DTB-drug compound after administration in vivo thiolytically decomposes to regenerate the amine-containing drug in its native, active form, therapeutic activity of the compound after modification and prior to administration is not necessary. Thus, in cases where modification of the drug with the DTB-polymer causes a reduction or loss of therapeutic activity, after administration and cleavage of the DTB-polymer from the drug, activity of the drug is regained.

Figure 13:
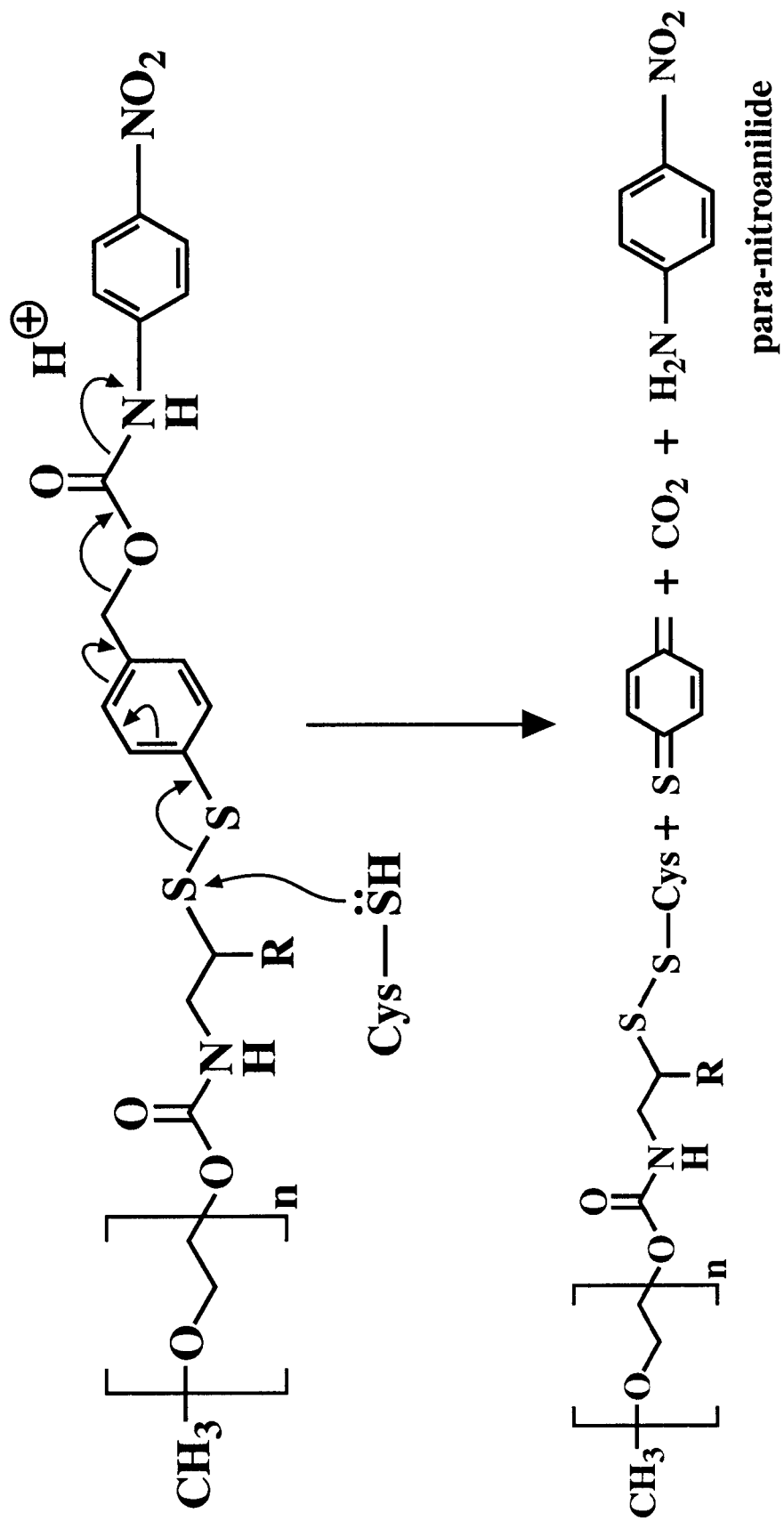
FIG. 13 shows the decomposition products after thiolytic cleavage of the an mPEG-DTB-p-nitroanilide conjugate.

In studies performed in support of the invention, the drug nitroanilide was reacted with mPEG-MeDTB-nitrophenylcarbonate to form an mPEG-MeDTB-para-nitroanilide compound, as shown in FIG. 13. Decomposition of the compound upon exposure to a reducing agent yields the products shown in the figure, with the drug para-nitroanilide regenerated in an unmodified state.

Figure 14A:
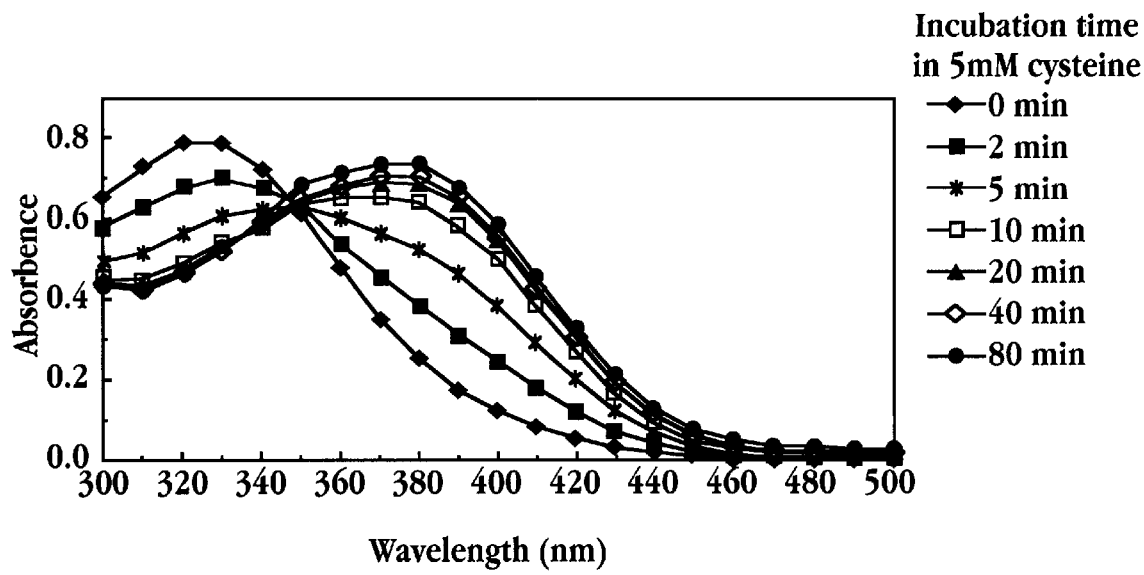
FIG. 14A shows the absorbence as a function of wavelength, in nm, of mPEG-MeDTB-para-nitroanilide (closed diamonds) and after in vitro incubation with 5 mM cysteine for 2 minutes (closed squares), 5 minutes (x symbols), 10 minutes (open squares), 20 minutes (triangles), 40 minutes (open diamonds) and 80 minutes (closed circles)

The mPEG-MeDTB-para-nitroanilide compound was incubated in vitro in buffer containing 5 $\mu$M cysteine and the absorbence of samples withdrawn at various times is shown in FIG. 14A. Seen in the figure are samples measured at the following time points: time zero (closed diamonds), 2 minutes (closed squares), 5 minutes (x symbols), 10 minutes (open squares), 20 minutes (triangles), 40 minutes (open diamonds) and 80 minutes (closed circles). The change in the UV spectra as a function of incubation time in cysteine is evident, showing cysteine-mediated release of para-nitroanilide from the mPEG-MeDTB-para-nitroanilide compound.

Figure 14B:
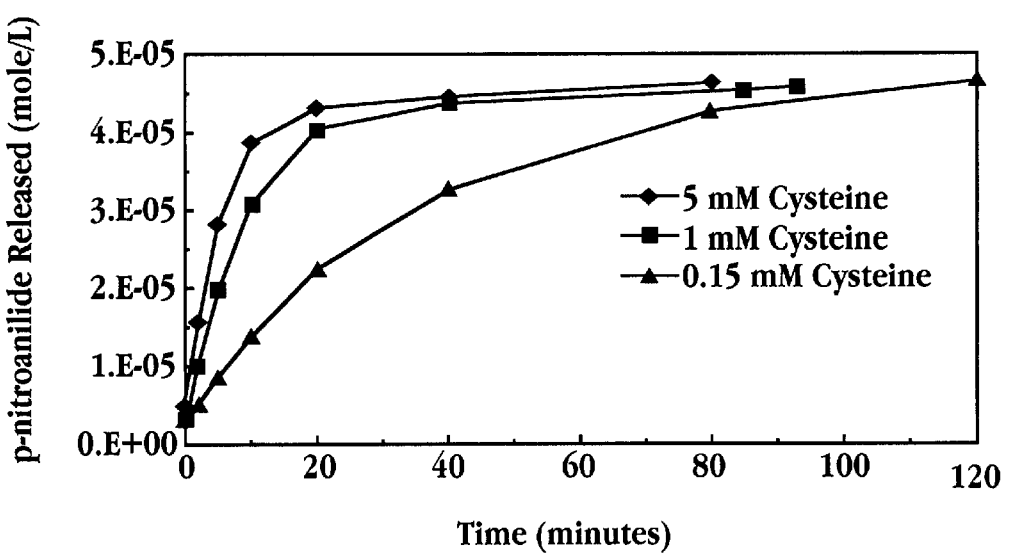
FIG. 14B shows the amount of para-nitroanilide, in mole/ L, released in vitro as a function of time, in minutes, from mPEG-MeDTB-para-nitroanilide conjugate incubated in the presence of 5 mM cysteine (closed circles), 1 mM cysteine (closed squares) and 0.15 mM cysteine (closed diamonds).

FIG. 14B shows the amount of para-nitroanilide, in mole/L, released in vitro from the mPEG-MeDTB-para-nitroanilide conjugate incubated in the presence of 5 mM cysteine (closed circles), 1 mM cysteine (closed squares) and 0.15 mM cysteine (closed diamonds). The rate of drug release from the conjugate was dependent on the concentration of reducing agent present.

From the foregoing, it can be seen how various objects and features of the invention are met. The compounds of the invention comprise an amine-containing ligand reversibly joined to a hydrophilic polymer via an ortho or para-disulfide of a benzyl urethane linkage. This linkage when subjected to mild thiolytic conditions is cleaved to regenerate the original amine-containing ligand in its unmodified form. The rate of cleavage can be controlled by steric hinderance of the disulfide in the linkage and/or by controlling the thiolytic conditions in vivo. The compounds prior to cleavage of the dithiobenzyl linkage are provided with an increased blood circulation lifetime, improved stability and reduced immunogenicity.

III. EXAMPLES

The following examples further illustrate the invention described herein and are in no way intended to limit the scope of the invention.

Materials

All materials were obtained from commercially suitable vendors, such as Aldrich Corporation.

Example 1

Synthesis of mPEG-DTB-DSPE mPEG-MeDTB-nitrophenylcarbonate (300 mg, 0.12 mmol, 1.29 eq) was dissolved in $CHCl_3$ (3 ml). DSPE (70 mg, 0.093 mol) and TEA (58.5 μl, 0.42 mmol, 4.5 eq) were added to PEG-solution, and was stirred at 50° C. (oil bath temp). After 15 minutes, TLC showed that the reaction didn't go to completion. Then two portions of TEA (10 μl, and 20 μl), and few portions of mPEG-MeDTB-nitrophenylcarbonate (50 mg, 30 mg, 10 mg) were added every after 10 minutes, until the reaction went to completion. Solvent was evaporated. Product mixture was dissolved in MeOH, and 1 g of C8 silica was added. Solvent was evaporated again. Product containing C8 silica was added on the top of the column, and was eluted with MeOH: $H_2O$ gradient (pressure), MeOH: $H_2O$=30:70, 60 ml; MeOH: $H_2O$=50:50, 60 ml; MeOH: $H_2O$=70:30, 140 ml (starting material eluted); MeOH: $H_2O$=75:25=40 ml; MeOH: $H_2O$= 80:20, 80 ml (product eluted); MeOH: $H_2O$=85:15, 40 ml; MeOH: $H_2O$=90:10, 40 ml; MeOH=40 ml; $CHCl_3$: MeOH: $H_2O$=90:18:10, 40 ml. Fractions containing pure product were combined and evaporated to give product as colorless thick liquid. Tertiary butanol (5 ml) was added to it, lyophilized and the dried in vacuo over $P_2O_5$ to give product as white fluffy solid (252 mg, 89% yield).

The ortho- and para-DTB-DSPE compounds were purified by silica gel chromatography (methanol gradient 0–10% in chloroform, ≈70% isolated yield) and the structures confirmed by NMR and MALDI-TOFMS. ($^1$H NMR for para conjugate: (d6-DMSO, 360 MHz) δ 0.86 (t, $CH_3$, 6 H), 1.22 (s, $CH_2$ of lipid, 56H), 1.57 (m, $CH_2CH_2CO_2$, 4H), 2.50 (2×t, $CH_2CO_2$, 4H), 2.82 (t, $CH_2S$, 2H), 3.32 (s, $OCH_3$, 3H), 3.51 (m, PEG, ≈180 H), 4.07 (t, PEG-$CH_2$OCONH, 2H), 4.11 & 4.28 (2×dd $CH_2$CH of glycerol, 2H), 4.98 (s, benzyl-$CH_2$, 2H), 5.09 (m, $CHCH_2$ of lipid), 7.35 & 7.53 (2×d, aromatic, 4H) ppm. The ortho conjugate differed only in benzyl and aromatic signals at 5.11 (s, $CH_2$, 2H), and 7.31 (d, 1H), 7.39 (m, 2H) 7.75 (d, 1H) ppm.

MALDI-TOFMS produced a distribution of ions spaced at equal 44 Da intervals, corresponding to the ethylene oxide repeating units. The average molecular weights of the compounds was 3127 and 3139 Da for para and ortho isomers respectively (theoretical molecular weight ~3100 Da).

The reaction scheme is illustrated in FIG. 2.

Example 2

Synthesis of mPEG-DTB-DSPE
A. mPEG-MeDTB-DSPE

This reaction scheme is illustrated in FIGS. 4A–4B.

mPEG(5K)-OH (40 g, 8 mmol) was dried azeotropically with toluene (total volume was 270 ml, 250 ml was distilled off by Dean-Stark). Dichloromethane (100 ml) was added to mPEG-OH. P-nitrophenyl chloroformate (2.42 g, 12 mmol, 1.5 eq), and TEA (3.3 ml, 24 mmol, 3 eq) were added to PEG solution at 4° C. (ice water), while taking precautions against moisture. Light yellow TEA hydrochloride salt was formed. After 15 minutes cooling bath was removed, and the reaction mixture was stirred at room temperature overnight. TLC showed ($CHCl_3$:MeOH:$H_2O$=90:18:2) that the reaction was complete. Solvent was evaporated. The residue was dissolved in ethyl acetate (~50° C.). TEA hydrochloride salt was filtered off and washed with warm ethyl acetate. Solvent was evaporated and the product recrystallized with isopropanol (three times). Yield: 38.2 g (92%). $^1$H NMR (DMSO-$d_6$, 360 MHz) δ 3.55 (s, PEG, 450H); 4.37 (t, PEG-$CH_2$, 2H); 7.55 (d, $C_6H_5$, 2H); 8.31 (d, $C_6H_5$, 2H).

1-Amino-2-propanol (1.1 ml, 14.52 mmol, 3 eq), and TEA (2.02 ml, 14.52 mmol, 3 eq) were added to mPEG (5K)-nitrophenyl carbonate (25 g, 4.84 mmol) in DMF (60 ml) and $CH_2Cl_2$ (40 ml). It was a yellow clear solution. The reaction mixture was stirred at room temperature for 30 minutes. TLC ($CHCl_3$:MeOH=90:10) showed that the reaction went to completion. Solvent (dichloromethane) was evaporated. Isopropanol (250 ml) was added to the product mixture in DMF (60 ml). Product precipitated immediately, and then recrystallized with iPrOH (three times). Yield: 22.12 g (90%). $^1$H NMR (DMSO-$d_6$, 360 MHz) δ 0.98 (d, $CH_3$CH(OH)$CH_2$, 3H); 3.50 (s, PEG, 180H); 4.03 (t, PEG-$CH_2$, 2H); 4.50 (d, $CH_3$CHOH, 1H); 7.0 (t, mPEG-OCONH).

mPEG(5K)-urethane-2-methyl propanol (22.12 g, 4.34 mmol) was dried azeotropically with toluene (45 ml). Dichloromethane (60 ml) was added to it. Methane sulfonyl chloride (604.6 μl, 7.81 mmol, 1.8 eq) and TEA (3.93 ml, 28.21 mmol, 6.5 eq) were added to mPEG-solution at 0° C. while maintaining stirring and taking precautions against moisture. After 30 minutes, cooling bath was removed, and the reaction mixture was stirred at room temperature for 16 h. Solvent was evaporated. Ethyl acetate was added to remove TEA salts. The product was recrystallized with isopropanol (three times). Yield: 20.27 g (90%). $^1$H NMR (DMSO-$d_6$, 360 MHz) δ 1.27 (d, $CH_3$CHO$SO_2CH_3$, 3H); 3.162 (s, $CH_3O_2$SOCH, 3H); 3.50 (s, PEG, 180H); 4.07 (t, PEG-$CH_2$, 2H); 4.64 (q, $CH_3$CHOH, 1H); 7.43 (t, mPEG-OCONH).

mPEG(5K)-urethane-2methyl-methane sulfone (10.27 g, 1.98 mmol) was dried azeotropically with toluene (20 ml, each time). Sodium hydride (377 mg, 9.4 mmol, 4.75 eq) was added in anhydrous toluene (60 ml) at 0° C. (in ice water). After 5 minutes, triphenylmethanethiol (3.92 g, 14.6 mmol, 7.15 eq) was added to the solution. After 10 minutes, mPEG-urethane-2methyl-methane sulfone (10.27 gm, 1.98 mmol) was added to the reaction mixture. It became a yellow solution. After 45 minutes, TLC ($CHCl_3$:MeOH:$H_2O$=90:18:2) showed that the reaction went to completion. Acetic acid (445.57 μl, 7.42 mmol, 3.75 eq) was added to the reaction mixture to neutralize excess of sodium hydride. The solution became thick and whitish. Solvent was evaporated and the solid was recrystallized with ethyl acetate (30 ml) and isopropanol (70 ml). The product mixture did not dissolve completely, while precipitate filtered off. Then the product mixture was recrystallyzed with isopropanol/tert-butyl alcohol (100 ml/20 ml). Yield: 8.87 g (84%). $^1$H NMR (DMSO-$d_6$, 360 MHz) δ 0.74 (d, $CH_3$CHSC($C_6H_5$)$_3$, 3H), 3.50 (s, PEG, 180H), 4.0 (t, PEG-$CH_2$, 2H), 4.64 (q, $CH_3$CHOH, 1H); 7.49 (t, mPEG-OCONH); 7.20–7.41 (m, SC($C_6$HS)$_3$, 15H).

mPEG(5K)-urethane-2methyl-triphenylmethanethiol (8.87 g, 1.65 mmol) was dissolved in TFA/$CH_2Cl_2$ (10 ml/10 ml) at 0° C. Under vigorous stirring, methoxy carbonylsulfenyl chloride (185.5 μl, 1.99 mmol, 1.2 eq) was added to the solution. The reaction mixture was stirred at room temperature for 15 minutes. TLC ($CHCl_3$:MeOH=90:10) showed that the reaction was complete. Solvents were evaporated. The product mixture was recrystallized with isopropanol:tert-butyl alcohol (80 ml:20 ml) two times. Tertiary butanol (5 ml) was added to the product, which was then lyophilized and dried in vacuo over $P_2O_5$ to give product as white fluffy solid (8.32g, 97% yield). $^1$H NMR (DMSO-$d_6$, 360 MHz) δ 1.17 (d, $CH_3$CHSSCOO$CH_3$, 3H); 3.42 (s, PEG, 180H); 3.84 (s, $CH_3$OCOSSCH, 3H); 4.05 (t, mPEG-$CH_2$, 2H); 7.38 (t, mPEG-OCONH, 1H).

mPEG(5K)-urethane ethyl(methyl)dithiocarbonyl methoxide (8.32 g, 1.6 mmol) was dissolved in dry methanol (20 ml), and chloroform (2.5 ml). A solution of mercapto benzyl alcohol (592 mg, 4 mmol, 2.5 eq) in dry methanol (2 ml) was added to the PEG-solution. The reaction mixture was stirred at room temperature for 18 h. Solvent was evaporated, product mixture was recrystallized with ethyl acetate/isopropanol, 30 ml/100 ml (3 times). NMR showed ~16% product was formed. So, another portion of mercapto benzyl alcohol (322 mg, 2.18 mmol, 1.8 eq) in MeOH (2 ml) was added dropwise to the product mixture in MeOH/CHCl$_3$ (24 ml/1 ml) at 0° C. (ice water). After addition (~10 minutes) completion, ice bath was removed, and the reaction mixture was stirred at room temperature for 24 h. TLC (CHCl$_3$:MeOH:H$_2$O=90:18:2) showed that the reaction was complete. Solvent was evaporated, and then product mixture was recrystallized with ethyl acetate/isopropanol, 30 ml/100 ml. Yield: 7.25 g, (94%). $^1$H NMR (DMSO-d$_6$, 360 MHz) δ 1.56 (d, CH$_3$CHSSC$_6$H$_5$CH$_2$OH, 3H); 3.29 (CH$_3$O-PEG, 3H); 3.50 (s, PEG, 450H); 4.03 (t, mPEG-CH$_2$, 2H); 4.46 (d, HOCH$_2$C$_6$H$_5$, 2H); 5.16 (t, HOCH$_2$C$_6$H$_5$, 1H); 7.30 (d, C$_6$H$_5$, 2H); 7.40 (br t, mPEG-OCONH, 1H); 7.50 (d, C$_6$H$_5$, 2H).

mPEG(5K)-urethane-ethyl(methyl)-dithiobenzyl alcohol (6.75 g, 1.27 mmol) was dissolved in CHCl$_3$ (30 ml), P-nitrophenyl chloroformate (513 mg, 2.54 mmol, 2 eq) was added to it at 0° C. (ice water). After 5 minutes triethylamine (531 μl, 3.81 mmol, 3 eq) was added. After 30 minutes ice bath was removed, and the reaction mixture was stirred at room temperature overnight. Solvent was evaporated. The product mixture was dissolved in ethyl acetate. TEA salt was filtered off, and then solvent was evaporated. Then the product mixture was recrystallized with ethyl acetate/isopropanol, 30 ml/100 ml (three times). Yield: 6.55 g (94%). $^1$H NMR (DMSO-d$_6$, 360 MHz) δ 1.17 (d, CH$_3$CHSSC$_6$H$_5$, 3H); 3.24 (CH$_3$O-PEG, 3H); 3.40 (s, PEG, 180H); 4.03 (br t, mPEG-CH$_2$, 2H); 5.28 (S, C$_6$H$_5$CH$_2$OCO, 2H); 7.45–8.35 (m, C$_6$H$_5$)$_2$, 8H).

mPEG-MeDTB-nitrophenylcarbonate (766 mg, 0.14 mmol, 1.29 eq) was dissolved in CHCl$_3$ (5 ml). DSPE (70 mg, 0.093 mol) and TEA (58.5 μl, 0.42 mmol, 4.5 eq) were added to PEG-solution, and was stirred at 50° C. (oil bath temp). After 20 minutes, TLC showed that the reaction didn't go to completion. More mPEG-MeDTB-nitrophenylcarbonate (total 1239 mg, 0.23 mmol, 2.47 eq) and 1-hydroxybenztriazole (HOBt) (25 mg, 0.19 mmol, 2 eq) were added. After 20 minutes, TLC (CHCl$_3$:MeOH:H$_2$O=90:18:2, with molybdenum and ninhydrin) showed that the reaction was complete. Solvent was evaporated. Product mixture was dissolved in warm (42° C.) ethyl acetate. It was a cloudy solution (TEA salt precipitated). The solution was filtered, and solvent was evaporated. MeOH, and 2 g of C8 silica was added to the product mixture. Solvent was evaporated again. Product containing C8 silica was added on the top of the column, and was eluted with MeOH:H$_2$O gradient (pressure), MeOH:H$_2$O 30:70, 100 ml; MeOH:H$_2$O 50:50, 100 ml; MeOH:H$_2$O 70:30, 250 ml (starting material eluted); MeOH:H$_2$O 75:25=40 ml; MeOH:H$_2$O 80:20, 200 ml (product eluted); MeOH=100 ml; CHCl$_3$:MeOH:H$_2$O= 90:18:2, 100 ml; CHCl$_3$:MeOH:H$_2$O=75:36:6, 100 ml. Fractions containing pure product were combined and evaporated to give product as colorless thick liquid. Tertiary butanol (5 ml) was added to it, lyophilized and then dried in vacua over P$_2$O$_5$ to give product as white fluffy solid (467 mg, 83% yield) $^1$H NMR (DMSO-d$_6$, 360 MHz) δ 0.83 (d, 2(CH$_3$), 3H); 1.16 (d, CH$_3$CHSSC$_6$H$_5$, 3H); 1.21 (s, 28(CH$_2$, 56H); 1.47 (br m, CH$_2$CH$_2$CO, 4H); 2.23 (2×t, CH$_2$CH$_2$CO, 4H); 3.50 (s, PEG, 180H); 4.04 (br t, mPEG-CH$_2$, 2H); 4.05 (trans d, PO$_4$CH$_2$CHCH$_2$, 1H); 4.24 (cis d, PO$_4$CH$_2$CHCH$_2$, 1H) 4.97 (s, C$_6$H$_5$CH$_2$OCO-DSPE, 2H); 5.03 (br s, (PO$_4$CH$_2$CH, 1H); 7.32 (d, C$_6$H$_5$, 2H); 7.53 (d, C$_6$H$_5$, 2H); 7.52 (br s, mPEG-OCONH, 1H). MALDI-TOFMS produced a bell shaped distribution of ions spaced at equal 44 Da intervals, corresponding to the ethylene oxide repeating units. The average molecular mass of the conjugate and mPEG-thiol (mostly cleaved disulfide) is 6376 and 5368 Da (theoretical molecular mass ~6053, and 5305 Daltons).

B. mPEG-ethylDTB-DSPE mPEG-urethane ethyl(ethyl)dithiocarbonyl methoxide (2 g, 0.90 mmol) was dissolved in dry methanol (8 ml). At the beginning the solution was cloudy, but after 5 minutes it became a clear solution. Mercaptobenzyl alcohol (265.2 mg, 1.79 mmol, 2 eq) was added to the PEG-solution. The reaction mixture was stirred at room temperature for 30 hours. Ether (70 ml) was added to the reaction solution to precipitate the product, and kept at 4° C. overnight. The white solid was filtered and recrystallized with ethyl acetate/ether, 30 ml/70 ml. Yield: 1.96 g, (94%). $^1$H NMR (DMSO-d$_6$, 360 MHz) 60.86 (d, CH$_3$CH$_2$CHSSC$_6$H$_5$CH$_2$OH, 3H); 1.42 (p, CH$_3$CH$_2$CHSSC$_6$H$_5$CH$_2$OH, 1H) 1.64 (p, CH$_3$CH$_2$CHSSC$_6$H$_5$CH$_2$OH, 1H); 3.51 (s, PEG, 180H); 4.03 (t, mPEG-CH$_2$, 2H); 4.47 (d, HOCH$_2$C$_6$H$_5$, 2H); 5.20 (t, HOCH$_2$C$_6$H$_5$, 1H) 7.31(d, C$_6$H$_5$, 2H); 7.42 (br t, mPEG-OCONH, 1H); 7.49 (d, C$_6$H$_5$, 2H).

N-hydroxy-s-norbornene-2,3-dicarboxylic acid imide (HONB) (48 mg, 0.269 mmol) was added to DSPE (55 mg, 0.073 mmol) in CHCl$_3$ (3 ml) at 50° C. (oil bath temperature). After 3–4 minutes it became a clear solution. Then mPEG-EtDTB-nitrophenylchloroformate (334 mg, 0.134 mmol) was added, followed by triethylamine (TEA, 45 μl, 0.329 mmol). After 20 minutes TLC (CHCl$_3$:MeOH:H$_2$O=90:18:2) showed that the reaction went to completion (molybdenum and ninhydrin sprays). Solvent was evaporated. Product mixture was dissolved in methanol, mixed with C8 silica (1 g) and striped of the solvent by rotary evaporation. The solid residue was added on the top of the C8-column, which was then eluted with MeOH:H$_2$O gradient (pressure), MeOH:H$_2$O=30:70, 60 ml; MeOH:H$_2$O=50:50, 60 ml; MeOH:H$_2$O=70:30, 140 ml; MeOH:H$_2$O=75:25=140 ml (starting material eluted); MeOH:H$_2$O=80:20, 80 ml; MeOH:H$_2$O=90:10, 140 ml (product eluted); MeOH=40 ml; CHCl$_3$:MeOH:H$_2$O= 90:18:10, 40 ml. Fractions containing pure product were combined and evaporated to give product as colorless thick liquid. Tertiary butanol (5 ml) was added, lyophilized and then dried in vacuo over P$_2$O$_5$ to give product as white fluffy solid (175 mg, 78% yield). $^1$H NMR (DMSO-d$_6$, 360 MHz) δ 0.85 (d, 2(CH$_3$), 6H; d, CH$_3$CHSSC$_6$H$_5$, 3H); 1.22 (s, 28(CH$_2$), 56H); 1.49 (br m, CH$_2$CH$_2$CO, 4H); 2.24 (2×t, CH$_2$CH$_2$CO, 4H); 3.50 (s, PEG, 180H); 4.04 (br t, mPEG-CH$_2$, 2H); 4.08 (trans d, PO$_4$CH$_2$CHCH$_2$, 1H); 4.27 (cis d, PO$_4$CH$_2$CHCH$_2$, 1H); 4.98 (s, C$_6$H$_5$CH$_2$OCO-DSPE, 2H); 5.06 (br s, (PO$_4$CH$_2$CH, 1H); 7.34 (d, C$_6$H$_5$, 2H); 7.53 (d, C$_6$H$_5$, 2H); 7.55 (br s, mPEG-OCONH, 1H).

Example 3

Synthesis of mPEG-DTB-nitrophenylchloroformate

A. Procedures for synthesis of 1-(mercaptomethyl) ethylammonium chloride 1. 2-Amino-1-methylethyl hydrogen sulfate. 1-Amino-2-propanol (22.53g, 0.3 mol) was vigorously stirred in an ice bath. Sulfuric acid (16.10 ml, 0.3 mol) was added very slowly, over the course of one hour. Thick vapors and a very viscous solution were formed in the flask. After addition was complete, the reaction was heated between 170° C. and 180° C., under reduced pressure, connected to the house vacuum. Upon heating, the reaction turned light brown. After all water was removed (approximately 1 hour) it was allowed to cool to room temperature. Upon cooling a brown, glassy solid was formed which would crystallize when triturated with methanol. It was dissolved in water (50 ml) at 60° C. Enough warm methanol was added to make the solution 80% methanol. Upon cooling, crystals formed which were then filtered and dried over $P_2O_5$. Yield: 17.17g (37%). $^1$H NMR ($D_6$-DMSO): δ 1.16 (d, $CH_3$, 3H); δ 2.78 (dd, $NH_3$—$CH_2$, 1H); δ 2.97 (dd, $NH_3$—$CH_2$, 1H); δ 4.41 (m, CH—$OSO_3$, $^1$H); δ 7.69 (s, $H_3N$, 3H). Melting point: 248°–250° C. (lit: 250° C.)

2. 5-Methylthiazolidine-2-thione. 2-Amino-1-methylethyl hydrogen sulfate (23.03 g, 148 mmol) and carbon disulfide (10.71 ml, 178 mmol, 1.2 eq.) were stirred in a 250 ml round-bottom-flask in 50% aqueous ethanol (40 ml). To this, sodium hydroxide (13.06 g, 327 mmol, 2.2 eq.) in 50% aqueous ethanol (50 ml) was added drop-wise, very slowly. Upon addition of sodium hydroxide, all starting materials dissolved and the solution turned orange. The reaction was refluxed (85° C.) for 40 minutes, after which time it turned bright yellow and a thick precipitate was formed. Ethanol was evaporated and then the aqueous solution was warmed and then filtered through a Buchner funnel to remove all water-soluble impurities. The remaining crystals were dissolved in warm ethanol and then warm water was added until the solution was 80% water. The mixture was allowed to cool and then refrigerated, yielding long, needle-like crystals. Yield: 14.64 g (75%). $^1$H NMR ($D_6$-DMSO): δ 1.33 (d, $CH_3$, 3H); δ 3.50 (m, $R_3$CH, 1H); δ 3.95 (dd, N—$CH_2$, 1H); δ 4.05 (m, N—$CH_2$, 1H); δ 10.05 (s, NH, 1H). Melting point: 92.5–93.5 (lit: 94–95).

3. 1-(mercaptomethyl)ethylammonium chloride. 5-Methylthiazolidine-2-thione (6.5 g, 49 mmol) was placed in a 250 ml round-bottom-flask. A solution of aqueous hydrochloric acid (40 ml, 18% in $H_2O$) was added and the flask was heated in an oil bath. The reaction refluxed (120° C.) for one week. Three times throughout the week 1 ml of concentrated hydrochloric acid was added. The reaction was monitored using TLC with ethyl acetate as eluent. They were visualized using UV, ninhydrin, and iodine vapors. Through most of the week the reaction was a heterogeneous mixture, with the starting material as oil which was denser than water. After one week the oil starting material was gone, although still visible on TLC. The reaction was removed from heat and allowed to cool to room temperature, and then was refrigerated to crystallize starting material. The crystallized starting material was filtered. Filtrate was evaporated and it was dried over $P_2O_5$ and NaOH to remove all water and HCl. The crude product was washed with two portions of diethyl ether (50 ml each) to remove all starting material. It was again dried over $P_2O_5$. Yield: 2.83 g (45%). $^1$H NMR ($D_6$-DMSO): δ 1.33 (d, $CH_3$, 3H); δ 2.92 (m, N—$CH_2$, 2H); δ 3.12 (m, SH, 1H); δ 3.18 (m, $R_3$—CH, 1H); δ 8.23 (bs, $NH_3$, 3H). Melting point: 80–82° C. (lit: 92–94).

The reaction scheme is illustrated in FIG. 5.

B. Synthesis of mPEG-ethyl-DTB-nitrophenylchloroformate 1. 2-Amino-1-ethylethyl hydrogen sulfate. 1-Amino-2-butanol (15 ml, 158 mmol) was vigorously stirred in a 100 ml round-bottom-flask in an ice bath. Sulfuric acid (8.43 ml, 158 mmol) was added very slowly, over the course of one hour. Thick vapors and a very viscous solution were formed in the flask. After addition was complete, the reaction was heated between 170° and 180° C., under reduced pressure, connected to the house vacuum. Upon heating, the reaction turned light brown. After all water was removed (approximately 1 hour) it was allowed to cool to room temperature. Upon cooling a brown, glassy solid was formed. It was dissolved in hot water (50 ml) and then placed in the refrigerator overnight. Upon cooling, crystals formed which were then filtered and dried over $P_2O_5$. Yield: 9.98 g (37%). $^1$H NMR ($D_6$-DMSO): δ 0.87 (t, $CH_3$, 3H); δ 1.51 (q, $CH_3$—$CH_2$, 2H); δ 2.82 (dd, $NH_3$—$CH_2$, 1H); δ 3.00 (dd, $NH_3$—$CH_2$, 1H); δ 4.21 (m, CH-$OSO_3$, 1H); δ 7.70 (s, $H_3N$, 3H).

2. 5-Ethylthiazolidine-2-thione. 2-Amino-1-ethyl-ethyl hydrogen sulfate (9.98 g, 59 mmol) and carbon disulfide (4.26ml, 71 mmol, 1.2 eq.) were stirred in a 100 ml round-bottom-flask in 50% aqueous ethanol (15ml). To this, sodium hydroxide (5.20 g, 130 mmol, 2.2 eq.) in 50% aqueous ethanol (20 ml) was added drop-wise, very slowly. Upon addition of sodium hydroxide, all starting materials dissolved and the solution turned orange. The reaction was refluxed (85° C.) for 40 minutes, after which time it turned bright yellow and a thick precipitate was formed. Ethanol was evaporated and then the aqueous solution was warmed and then filtered through a Buchner funnel to remove all water-soluble impurities. The remaining crystals were dissolved in warm ethanol and then warm water was added until the solution was 80% water. The mixture was allowed to cool and then refrigerated, yielding needle-like crystals. Yield: 7.28g (86%). $^1$H NMR ($D_6$-DMSO): δ 0.88 (t, $CH_3$, 3H); δ 1.66 (in, $CH_3$—$CH_2$, 2H); δ 3.58 (m, $R_3$CH, 1H); δ 3.93 (m, N—$CH_2$, 2H); δ 10.06 (s, NH, 1H). Melting point: 76–78° (lit: 76.6–76.9).

3. 1-(mercaptoethyl)ethylammonium chloride. 5-Ethylthiazolidine-2-thione (7.24 g, 50 mmol) was placed in a 250 ml round-bottom-flask. A solution of aqueous hydrochloric acid (45 ml, 18% in $H_2O$) was added and the flask was heated in an oil bath. Upon heating, the starting material melted, forming, all heterogeneous mixture. The reaction refluxed (120° C.) for one week. Four times throughout the week 1 ml of concentrated hydrochloric acid was added. The reaction was monitored using TLC with ethyl acetate as eluent. They were visualized using UV, ninhydrin, and iodine vapors. Throughout the week the reaction was a heterogeneous mixture, with the starting material as oil which was denser than water. The reaction was removed from heat and allowed to cool to room temperature, and then was refrigerated to crystallize starting material. The crystallized starting material was filtered. Filtrate was evaporated and it was dried over $P_2O_5$ and NaOH to remove all water and HCl. The crude product was washed with two portions of diethyl ether (50 ml each) to remove all starting material. It was again dried over $P_2O_5$. Yield: 3.66 g (52%). $^1$H NMR ($D_6$-DMSO):

The reaction scheme is illustrated in FIG. 5.

Example 4

Synthesis of mPEG-DTB-lipid 1,2-distereoyl-sn-glycerol (500 mg, 0.8 mmol) was dried azeotropically with benzene (3 times). Para-nitrophenyl chloroformate (242 mg, 1.2 mmol, 1.5 eq), dimethylaminopyridine (DMAP) (10 mg, 0.08 mmol, 0.1 eq), and TEA (334.5 μl, 2.4 mmol, 3 eq) were added to 1,2-distereoyl glycerol in $CHCl_3$ (5 ml). The reaction mixture was stirred at room temperature for 2 h. TLC (Toluene: ethyl acetate= 7:3) showed that the reaction was complete. Then the product mixture was extracted with 10% citric acid to remove dimethylaminopyridine (DMAP), washed with acetonitrile (3 ml, 4 times) to remove excess of p-nitrophenyl chloroformate. Pure product was dried in vacuo over $P_2O_5$. Yield: 557 mg(88%). %). $^1$H NMR (CHCl$_3$, 360 MHz) δ 0.88 (t, end CH$_3$, 6H); 1.25 (s, 28×CH$_2$, 56H); 1.58 (m, CH$_2$CH$_2$CO, 4H); 2.34 (2×t, CH$_2$CO, 4H); 4.22 (trans d, CH$_2$OCOC$_{17}$H$_{35}$, 1H); 4.35 (m, OCOOCH$_2$CH, 2H); 4.51 (cis d, CH$_2$OCOC$_{17}$H$_{35}$, 1H); 5.37 (m, OCOOCH$_2$CH, 1H); 7.39 (d, C$_6$H$_5$, 2H); 8.28 (d, C$_6$H$_5$, 2H).

Ethylene diamine (42 μl, 0.63 mmol, 5 fold excess), and pyridine (200 μl, were added in CHCl$_3$ (1 ml). 2-disteroyl-sn-p-nitrophenyl carbonate (100 mg, 0.13 mmol) was dissolved in CHCl$_3$ (1 ml) and added dropwise to ethylene diamine solution with a pastuer pipette at 0° C. (ice water) and continued overnight (16 h). TLC (CHCl$_3$:MeOH:H$_2$O 90:18:2, and CHCl$_3$:MeOH=90:10) showed that the reaction was complete. Solvent was evaporated to remove pyridine. Then the product mixture was dissolved in CHCl$_3$, loaded onto the column (Aldrich, Silica gel, 60° A, 200–400 mesh), and eluted with CHCl$_3$: CH$_3$COCH$_3$, and CHCl$_3$:MeOH gradient, CHCl$_3$: CH$_3$COCH$_3$=90:10, 60 ml (upper spot eluted); CHCl$_3$:NeOH=90:10, 60 ml (product eluted). Fractions containing pure product were combined and evaporated. Tert-butanol was added and dried in vacuo over $P_2O_5$. Yield: 64 mg (75%). $^1$H NMR (DMSO-d$_6$, 360 MHz) δ 0.83 (t, end CH$_3$, 6H); 1.22 (s, 28×CH$_2$, 56H); 1.51 (m, CH$_2$CH$_2$CO, 4H); 2.25 (2×t, CH$_2$CO, 4H); 2.83 (m, H$_2$NCH$_2$CH$_2$NH, 2H); 3.21 (m, H$_2$NCH$_2$CH$_2$NH, 2H); 4.10–4.14 (m & cis d, COOCH$_2$CHCH$_2$, 4H); 5.17 (m, OCOOCH$_2$CH, 1H); 7.78 (m, H$_2$NCH$_2$CH$_2$NH, 2H).

mPEG-MeDTB-nitrophenylchloroformate (400 mg, 0.162 mmol, 2.2 eq) was dissolved in CHCl$_3$ in (2 ml). 1,2-steroyl-sn-ethylene amine (51 mg, 0.075 mmol) and TEA (37 μl, 0.264 mmol, 3.52 eq) were added to the solution. Then the reaction mixture was stirred at 45° C. for 20 minutes. TLC (CHCl$_3$:MeOH:H$_2$O=90:18:2, and CHCl$_3$:MeOH=90:10) showed that the reaction went to completion. Solvent was evaporated. The product mixture was dissolved in methanol. 2 g of C8 silica was added and then solvent was evaporated. C8 silica containing product mixture was added on the top of the C8 column ((Supelco, Supel clean. Lot no. SP0824), and was eluted with MeOH:H$_2$O gradient (pressure), MeOH:H$_2$O=60:40, 40 ml; MeOH:H$_2$O=70:30, 80 ml (starting material eluted); MeOH:H$_2$O=80:20, 40 ml; MeOH:H$_2$O=90:10=20 ml; CHCl$_3$:MeOH:H$_2$O=5:80:15, 20 mi; CHCl$_3$:MeOH:H$_2$O= 90:18:10, 40 ml (product eluted). Fractions containing pure product were combined and evaporated to give product as colorless thick liquid. Tertiary butanol (5 ml) was added and the solution was lyophilized and then dried in vacuo over $P_2O_5$ to give product as white solid (200 mg, 89% yield) $^1$H NMR (DMSO-d$_6$, 360 MHz) δ δ 0.83 (t, end CH$_3$, 6H); 1.22 (s, 28×CH$_2$, 56H); 1.48 (m, CH$_2$CH$_2$CO, 4H); 2.25 (2×t, CH$_2$CO, 4H); 3.10 (m, HNCH$_2$CH$_2$NH, 4H); 3.50 (s, PEG, 180H); 4.04 (t, mPEG-CH$_2$, 2H); 4.09 (trans d, COOCH$_2$CHCH$_2$, 1H); 4.25 (cis d, COOCH$_2$CHCH$_2$, 1H); 4.98 (s, C$_6$H$_5$CH$_2$OCO, 2H); 5.23 (m, COOCH$_2$CHCH$_2$, 1H); 7.18 (m, NHCH$_2$CH$_2$NH, 2H); 7.33 (d, C$_6$H$_5$, 2H); 7.38 (m, mPEG-OCONH, 1H); 7.52 (d, C$_6$H$_5$, 2H).

The reaction scheme is illustrated in FIG. 6A.

Example 5

In vitro Cleavage of mPEG-DTB-DSPE Compound

Ortho-mPEG-DTB-DSPE and para-mPEG-DTB-DSPE (prepared as described in Example 1) were added to a buffered aqueous solution (pH 7.2) in the presence and absence of 150 μM cysteine. Disappearance of the conjugates was monitored by HPLC (Phenomenex C$_8$ Prodigy, 4.6×50 mm column, detection at 277 nm, mobile phase methanol/water 95:5 with 0.1% trifluoroacetic acid at 1 mL/min). The results are illustrated in FIG. 7A where the ortho-conjugate is represented by the open circles and the para-conjugate by the open squares.

Example 6

In vitro Cleavage of o- and p-mPEG-DTB-DSPE Compound in Liposomes

A. Liposome Preparation

The lipids partially hydrogenated phosphatidylcholine (PHPC), cholesterol and ortho- or para-mPEG-DTB-DSPE (prepared as described in Example 1, mPEG MW=1980 Daltons) were dissolved in a 95:5:3 molar ratio, respectively, in a suitable organic solvent, typically cholorform/methanol in a 1:1 or 1:3 ratio. The solvent was removed by rotary evaporation to form a dried lipid film. The film was hydrated with aqueous buffer to from liposomes that were sized via extrusion to an average diameter of 120 nm.

B. In vitro Characterization

The liposomes were incubated in phosphate buffered saline, pH 7.2, containing 5 μM EDTA at 37° C. in the presence of 150 μM cysteine. Disappearance of the conjugates was monitored by HPLC (Phenomenex C$_8$ Prodigy, 4.6×50 mm column, detection at 277 nm, mobile phase methanol/water 95:5 with 0.1% trifluoroacetic acid at 1 mL/min). Results are shown in FIG. 7B where the liposomes comprising the ortho-conjugate are represented by the solid circles and liposomes comprising the para-conjugate by the solid squares. The open circles and the open squares correspond to ortho-mPEG-DTB-DSPE and para-mPEG-DTB-DSPE in micellar form (discussed above in Example 5, FIG. 7A).

Example 7

In vitro Cleavage of o- and p-mPEG-DTB-DSPE Compound in Liposomes

A. Liposome Preparation

The lipids dioleoyl phosphatidylethanolamine (DOPE) and ortho- or para-mPEG-DTB-DSPE (prepared as described in Example 1, mPEG MW=1980 Daltons) were dissolved a 97:3 molar ratio in chloroform/methanol 1:1. The solvent was removed by rotary evaporation to form a dried lipid film. The lipid film was hydrated with an aqueous solution containing 30 mM each of the fluorophores p-xylene-bis-pyridinium bromide and trisodium 8-hydroxypyrenetrisulfonate. was hydrated with aqueous buffer to from liposomes that were sized via extrusion to an average diameter of 100 nm.

B. In vitro Characterization

The liposomes were incubated in HEPES buffer, pH 7.2, at 37° C. in the presence of cysteine at concentrations of 15 μM, 150 μM, 300 mM and 1.5 μM. Percent of released dye was determined as the increase in sample fluorescence ($\lambda_{em}$=512 nm, $\lambda_{ex}$=41$^3$ nm pH-independent isobestic point) over that of the preincubation sample (zero release) normalized to the increase in fluorescence obtained after lysis of preincubation sample with 0.2% Triton X-100 (100% release) (Kirpotin, D. et al., FEBS Letters, 388:115–118 (1996)). Results at various cysteine concentrations for liposome comprising the ortho-compound are shown in FIG. 8A and for the for the para-compound are shown in FIG. 8B.

Example 8

In vivo Characterization of Liposomes comprising mPEG-DTB-DSPE Compound

A. Liposome Preparation

The lipids partially hydrogenated phosphatidylcholine (PHPC), cholesterol and para-mPEG-DTB-DSPE (prepared as described in Example 1, mPEG MW=1980 Daltons) were dissolved in a 55:40:5 mole percent ratio, respectively, in an organic solvent. The solvent was removed by rotary evaporation to form a dried lipid film. The film was hydrated with aqueous buffer containing diethylene triamine pentacetic acid (EDTA) to form liposomes. After downsizing the liposomes to an average diameter of 120 nm unentrapped EDTA was removed and $In^{111}$ was added to the external medium. The liposomes were incubated for a time sufficient for $In^{111}$ to cross the lipid bilayer and chelate with EDTA.

B. In vivo Administration

Mice were divided into two study groups. The liposome composition described above was injected into all test animals. One group of the test animals also received a 200 µL injection of 200 µM cysteine at 1, 3 and 5 hours post liposome injection. The other test group received an injection of saline at the same time points. Liposome content in the blood was determined by monitoring blood samples for $In^{111}$. The results are shown in FIG. 10.

Although the invention has been described with respect to particular embodiments, it will be apparent to those skilled in the art that various changes and modifications can be made without departing from the invention.

It is claimed:

1. A compound having the general structure:

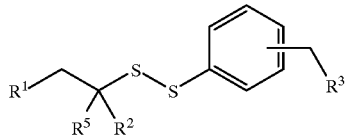

wherein $R^1$ is a hydrophilic polymer comprising a linkage for attachment to the dithiobenzyl moiety; $R^2$ is selected from the group consisting of H, alkyl and aryl; $R^3$ is selected from the group consisting of $O(C=O)R^4$, $S(C=O)R^4$, and $O(C=S)R^4$; $R^4$ comprises an amine-containing ligand; and $R^5$ is selected from the group consisting of H, alkyl and aryl; and where orientation of $CH_2$—$R^3$ is selected from the ortho position and the para position.

2. The compound of claim 1, wherein $R^5$ is H and $R^2$ is selected from the group consisting of $CH_3$, $C_2H_5$ and $C_3H_8$.

3. The compound of claim 1, wherein the amine-containing ligand $R^4$ is selected from the group consisting of a polypeptide, an amine-containing drug and an amine-containing lipid.

4. The compound of claim 1, wherein the amine-containing ligand $R^4$ is an amine-containing lipid comprising either a single hydrocarbon tail or a double hydrocarbon tail.

5. The compound of claim 4, wherein the amine-containing lipid is a phospholipid having a double hydrocarbon tail.

6. The compound of claim 1, wherein $R^2$ and $R^5$ are alkyls.

7. The compound of claim 1, wherein $R^1$ is selected from the group consisting of polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethyleneglycol, polyaspartamide, copolymers thereof, and polyethyleneoxide-polypropylene oxide.

8. The compound of claim 1, wherein $R^1$ is polyethyleneglycol.

9. The compound of claim 8, wherein $R^5$ is H and $R^2$ is $CH_3$ or $C_2H_5$.

10. A liposome comprising the compound of claim 1.

11. A liposome comprising the compound of claim 9.

12. The compound of claim 1, wherein the amine-containing ligand $R^4$ is a polypeptide.

13. The compound of claim 12, wherein the polypeptide is a recombinant polypeptide.

14. The compound of claim 7, wherein the polypeptide is a recombinant polypeptide.

15. The compound of claim 12, wherein the polypeptide is a cytokine.

16. The compound of claim 12, wherein the polypeptide is selected from the group consisting of interferons, interleukins, growth factors, and enzymes.

17. A composition comprising a conjugate obtainable by reaction with a compound having the general structural formula:

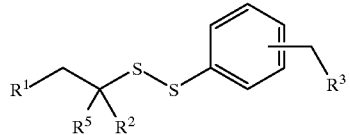

wherein $R^1$ is a hydrophilic polymer comprising a linkage for attachment to the dithiobenzyl moiety; $R^2$ is selected from the group consisting of H, alkyl and aryl; $R^3$ is selected from the group consisting of $O(C=O)R^4$, $S(C=O)R^4$, and $O(C=S)R^4$; $R^4$ comprises a leaving group; and $R^5$ is selected from the group consisting of H, alkyl and aryl; and where orientation of $CH_2$—$R^3$ is selected from the ortho position and the para position; and a pharmaceutically-acceptable carrier.

18. The composition of claim 17, wherein $R^2$ is selected from the group consisting of $CH_3$, $C_2H_5$ and $C_3HB_8$.

19. The composition of claim 17, wherein $R^3$ is $O(C=O)R^4$ and $R^4$ is a hydroxy- or oxy-containing leaving group.

20. The composition of claim 17, wherein the leaving group is derived from a compound selected from the group consisting of chloride, para-nitrophenol, ortho-nitrophenol, N-hydroxytetrahydrophthalimide, N-hydroxysuccinimide, N-hydroxyglutarimide, N-hydroxynorbornene-2,3-dicarboxyimide, 1-hydroxybenzotriazole, 3-hydroxypyridine, 4-hydroxypyridine, 2-hydroxypyridine, 1-hydroxy-6-trifluoromethylbenzotriazole, immidazole, triazole, N-methyl-imidazole, pentafluorophenol, trifluorophenol and trichlorophenol.

21. The composition of claim 17, wherein said compound is reacted with an amine-containing ligand that displaces $R^4$ to form a conjugate comprising said amine-containing ligand.

22. The composition of claim 21, wherein the amine-containing ligand comprises a phospholipid.

23. The composition of claim 22, wherein $R^1$ is selected from the group consisting of polyvinylpyrrolidone, polyvinylmethylether, polymethyloxazoline, polyethyloxazoline, polyhydroxypropyloxazoline, polyhydroxypropyl-methacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide, copolymers thereof, and polyethyleneoxide-polypropylene oxide.

24. The composition of claim 22, wherein $R^1$ comprises polyethyleneglycol.

25. The composition of claim 24, wherein $R^2$ is $CH_3$ or $C_2H_5$.

26. The composition of claim 25, wherein the composition containing the conjugate comprises a liposome.

27. The composition of claim 26, wherein the liposome further comprises an entrapped therapeutic agent.

28. The composition of claim 21, wherein the amine-containing ligand comprises a polypeptide.

29. The composition of claim 28, wherein $R^1$ is selected from the group consisting of polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethyleneglycol, polyaspartamide, copolymers thereof, and polyethyleneoxide-polypropylene oxide.

30. The composition of claim 28, wherein $R^1$ comprises polyethyleneglycol.

31. The composition of claim 30, wherein the polypeptide comprises a recombinant polypeptide.

32. The composition of claim 30, wherein the polypeptide comprises a cytokine.

33. The composition of claim 30, wherein the polypeptide is selected from the group consisting of interferons, interleukins, growth factors, and enzymes.

34. A liposome composition comprising:
liposomes comprising a surface coating of hydrophilic polymer chains wherein at least a portion of the hydrophilic polymer chains have the general structure:

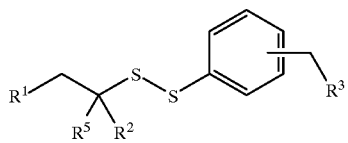

wherein $R^1$ is a hydrophilic polymer comprising a linkage for attachment to the dithiobenzyl moiety; $R^2$ is selected from the group consisting of H, alkyl and aryl; $R^3$ is selected from the group consisting of $O(C=O)R^4$, $S(C=O)R^4$, and $O(C=S)R^4$; $R^4$ comprises an amine-containing ligand; and $R^5$ is selected from the group consisting of H, alkyl and aryl; and where orientation of $CH_2-R^3$ is selected from the ortho position and the para position,
wherein the liposomes have a longer blood circulation lifetime than liposomes having hydrophilic polymer chains joined to the liposome via an aliphatic disulfide linkage.

35. The composition of claim 34, wherein $R^2$ is selected from the group consisting of $CH_3$, $C_2H_5$ and $C_3H_8$.

36. The composition of claim 34, wherein the amine-containing lipid comprises a phospholipid.

37. The composition of claim 36, wherein $R^1$ is selected from the group consisting of polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethyleneglycol, polyaspartamide, copolymers thereof, and polyethyleneoxide-polypropylene oxide.

38. The composition of claim 36, wherein $R^1$ comprises polyethyleneglycol.

39. The composition of claim 38, wherein $R^2$ is $CH_3$ or $C_2H_5$.

40. The composition of claim 34, wherein the liposome further comprises an entrapped therapeutic agent.

41. A method for improving the blood circulation lifetime of liposomes having a surface coating of releasable hydrophilic polymer chains, comprising
preparing liposomes that include between about 1% to about 20% of a compound having the general structure:

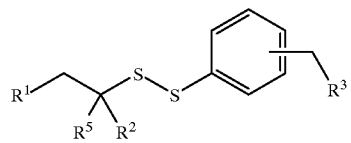

wherein $R^1$ is a hydrophilic polymer comprising a linkage for attachment to the dithiobenzyl moiety; $R^2$ is selected from the group consisting of H, alkyl and aryl; $R^3$ is selected from the group consisting of $O(C=O)R^4$, $S(C=O)R^4$, and $O(C=S)R^4$; $R^4$ comprises an amine-containing lipid; and $R^5$ is selected from the group consisting of H, alkyl and aryl; and where orientation of $CH_2-R^3$ is selected from the ortho position and the para position.

42. The method of claim 41, wherein $R^5$ is H and $R^2$ is selected from the group consisting of $CH_3$, $C_2H_5$ and $C_3H_8$.

43. The method of claim 41, wherein the amine-containing lipid comprises a phospholipid.

44. The method of claim 43, wherein $R^1$ is selected from the group consisting of polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethyleneglycol, polyaspartamide, copolymers thereof, and polyethyleneoxide-polypropylene oxide.

45. The method of claim 43, wherein $R^1$ comprises polyethyleneglycol.

46. The method of claim 45, wherein $R^2$ is $CH_3$ or $C_2H_5$.

47. The method of claim 41, wherein the liposome further comprises an entrapped therapeutic agent.

* * * * *

UNITED STATES PATENT AND TRADEMARK OFFICE
CERTIFICATE OF CORRECTION

PATENT NO.    : 6,342,244 B1
DATED         : January 29, 2002
INVENTOR(S)   : Samuel Zalipsky It is certified that error appears in the above-identified patent and that said Letters Patent is hereby corrected as shown below:

Column 26,
Line 18, please delete "the polypeptide" amd insert -- $R^4$ -- in its place.

Signed and Sealed this

Twenty-sixth Day of October, 2004

JON W. DUDAS
*Director of the United States Patent and Trademark Office*

(12) EX PARTE REEXAMINATION CERTIFICATE (4917th)
United States Patent
Zalipsky

(10) Number: US 6,342,244 C1
(45) Certificate Issued: Mar. 9, 2004

(54) RELEASABLE LINKAGE AND COMPOSITIONS CONTAINING SAME

(75) Inventor: Samuel Zalipsky, Redwood City, CA (US)

(73) Assignee: Alza Corporation, Mountain View, CA (US)

Reexamination Request:
No. 90/006,553, Feb. 21, 2003

Reexamination Certificate for:
Patent No.: 6,342,244
Issued: Jan. 29, 2002
Appl. No.: 09/556,056
Filed: Apr. 21, 2000

Related U.S. Application Data
(60) Provisional application No. 60/130,897, filed on Apr. 23, 1999, now abandoned.

(51) Int. Cl.$^7$ .................. A61K 9/127; A61K 45/00; A61K 38/00; A01N 61/00; C25D 3/60

(52) U.S. Cl. .................. 424/450; 424/85.1; 205/254; 514/1; 530/336; 536/84

(58) Field of Search ............... 424/450, 85.1; 205/254; 514/1; 530/336; 536/84

(56) References Cited

FOREIGN PATENT DOCUMENTS

EP       0 317 957 A2    5/1989

OTHER PUBLICATIONS

Kirpotin, D., et al., *FEBS Letters* 388:115–118, (1996).
Senter, P.D., et al., *J Org Chem* 55(9):2975–2978, (1990).

*Primary Examiner*—Jeffrey Siew

(57) ABSTRACT

A compound comprised of a hydrophilic polymer covalently yet reversibly linked to a amine-containing ligand through a dithiobenzyl linkage is described.

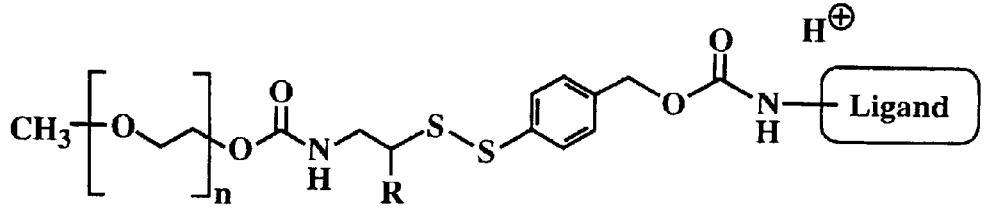

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–47 is confirmed.

* * * * *